(12) United States Patent
Best et al.

(10) Patent No.: US 11,259,947 B2
(45) Date of Patent: Mar. 1, 2022

(54) ANKLE BRACE DEVICES, SYSTEMS AND METHODS

(71) Applicant: Shock Doctor, Inc., Fountain Valley, CA (US)

(72) Inventors: William Best, Huntington Beach, CA (US); Thierry Petelle, Montreal (CA); Bastien Jourde, Montreal (CA)

(73) Assignee: Shock Doctor, Inc., Fountain Valley, CA (US)

( * ) Notice: Subject to any disclaimer, the term of this patent is extended or adjusted under 35 U.S.C. 154(b) by 525 days.

(21) Appl. No.: 16/207,613

(22) Filed: Dec. 3, 2018

(65) Prior Publication Data

US 2019/0099282 A1    Apr. 4, 2019

Related U.S. Application Data

(63) Continuation of application No. PCT/US2016/035853, filed on Jun. 3, 2016.

(51) Int. Cl.
*A61F 5/00* (2006.01)
*A61F 5/01* (2006.01)
*A61F 5/30* (2006.01)

(52) U.S. Cl.
CPC .............. *A61F 5/0111* (2013.01); *A61F 5/30* (2013.01)

(58) Field of Classification Search
CPC .. A61F 5/0111; A61F 5/01; A61F 5/03; A61F 5/0127; A61F 5/00; A61F 5/0104; A61F 5/0102; A61F 5/30; A61F 5/32; A61F 5/34; A61F 5/37; A61F 5/3761; A61F 5/058; A61F 13/00; A61F 13/06; A61F 13/064; A61F 13/066; A61F 13/067; A61F 2005/0174
See application file for complete search history.

(56) References Cited

U.S. PATENT DOCUMENTS 2,590,648 A     3/1952  Pitz
3,674,023 A     7/1972  Mann
(Continued)

FOREIGN PATENT DOCUMENTS

DE          8522310 U1      9/1985
DE     102006041195 A1      3/2008
(Continued)

OTHER PUBLICATIONS

International Preliminary Report on Patentability received for PCT Patent Application No. PCT/US2013/060152, dated Mar. 26, 2015, 7 pages.

(Continued)

*Primary Examiner* — Kim M Lewis
(74) *Attorney, Agent, or Firm* — Faegre Drinker Biddle & Reath LLP

(57) ABSTRACT

An ankle brace including an ankle wrap assembly including a main body having an inner surface, an outer surface, a top, a bottom, a front defining a foot opening, a first side panel, a second side panel, a rear, and a bottom panel. The ankle brace includes first and second ankle pads attached to the main body; a first support attached to the main body first side panel, and a second attached to the main body second side panel, and a bottom support. The ankle brace is configured to be secured to a user's ankle when worn.

18 Claims, 20 Drawing Sheets

(56) References Cited

U.S. PATENT DOCUMENTS

| | | | |
|---|---|---|---|
| 4,523,394 A | 6/1985 | Lindh et al. | |
| RE33,395 E | 10/1990 | Peters | |
| 4,977,891 A | 12/1990 | Grim | |
| 5,000,195 A | 3/1991 | Neal | |
| 5,031,607 A | 7/1991 | Ricke | |
| 5,067,486 A | 11/1991 | Hely | |
| 5,090,404 A * | 2/1992 | Kallassy | A61F 13/066 602/23 |
| 5,209,722 A | 5/1993 | Miklaus et al. | |
| 5,366,439 A | 11/1994 | Peters | |
| 5,429,588 A | 7/1995 | Young et al. | |
| 5,445,602 A | 8/1995 | Grim et al. | |
| 5,454,382 A | 10/1995 | Tariah et al. | |
| 5,496,263 A | 3/1996 | Fuller et al. | |
| 5,501,659 A | 3/1996 | Morris et al. | |
| 5,507,720 A | 4/1996 | Lampropoulos | |
| 5,527,269 A | 6/1996 | Reithofer | |
| 5,630,792 A | 5/1997 | Neal | |
| 5,676,642 A | 10/1997 | Peters | |
| D391,640 S | 3/1998 | Oviedo, Jr. | |
| 5,795,316 A * | 8/1998 | Gaylord | A61F 5/0111 602/27 |
| 5,797,865 A | 8/1998 | McDavid, III | |
| 5,836,903 A | 11/1998 | Peters | |
| 5,897,520 A * | 4/1999 | Gerig | A61F 5/0111 602/27 |
| 5,902,259 A | 5/1999 | Wilkerson | |
| 5,944,678 A | 8/1999 | Hubbard | |
| 5,951,504 A | 9/1999 | Iglesias et al. | |
| 5,966,843 A | 10/1999 | Sand et al. | |
| 5,971,946 A | 10/1999 | Quinn et al. | |
| D418,259 S | 12/1999 | Morton | |
| 6,053,884 A | 4/2000 | Peters | |
| 6,146,350 A | 11/2000 | Morton | |
| D436,177 S | 1/2001 | Miller | |
| 6,270,468 B1 | 8/2001 | Townsend et al. | |
| 6,272,772 B1 | 8/2001 | Sherman | |
| 6,299,587 B1 | 10/2001 | Birmingham | |
| 6,524,266 B1 | 2/2003 | Peters | |
| 6,602,215 B1 | 8/2003 | Richie, Jr. | |
| 6,656,145 B1 | 12/2003 | Morton | |
| 6,739,077 B2 | 5/2004 | Morgan | |
| 6,749,578 B2 | 6/2004 | Peters | |
| 6,767,332 B1 | 7/2004 | Pardue et al. | |
| 6,772,541 B1 | 8/2004 | Ritter et al. | |
| 6,792,700 B2 | 9/2004 | Gallegos | |
| 6,858,017 B2 | 2/2005 | Peters | |
| 7,014,621 B2 | 3/2006 | Nelson | |
| 7,020,989 B2 | 4/2006 | Kim | |
| 7,081,102 B1 | 7/2006 | Koetter et al. | |
| 7,267,656 B2 | 9/2007 | Cooper | |
| D552,743 S | 10/2007 | Verkade et al. | |
| RE40,215 E | 4/2008 | Cummings et al. | |
| 7,364,561 B1 | 4/2008 | Morton | |
| 7,370,442 B2 | 5/2008 | Jung et al. | |
| 7,429,254 B1 | 9/2008 | Engelman | |
| 7,587,841 B2 | 9/2009 | Culpepper | |
| 7,615,026 B1 | 11/2009 | Peters et al. | |
| 7,713,224 B1 | 5/2010 | Peters et al. | |
| D618,359 S | 6/2010 | Einarsson | |
| D620,124 S | 7/2010 | Einarsson | |
| 7,753,865 B1 | 7/2010 | Hely | |
| 7,785,283 B1 | 8/2010 | Bledsoe | |
| 7,828,758 B2 | 11/2010 | Clements et al. | |
| 8,007,454 B1 * | 8/2011 | Zerr | A61F 5/0111 602/23 |
| D663,852 S | 7/2012 | Joseph | |
| D672,878 S | 12/2012 | Einarsson | |
| D673,280 S | 12/2012 | Einarsson | |
| D696,409 S | 12/2013 | Best et al. | |
| 8,734,371 B2 | 5/2014 | Robertson | |
| D708,344 S | 7/2014 | Best et al. | |
| 2001/0015023 A1 | 8/2001 | Funk | |
| 2001/0054240 A1 | 12/2001 | Bordin et al. | |
| 2001/0056251 A1 | 12/2001 | Peters | |
| 2002/0055696 A1 | 5/2002 | Borsoi | |
| 2002/0062579 A1 | 5/2002 | Caeran | |
| 2003/0014001 A1 | 1/2003 | Martin | |
| 2003/0154627 A1 | 8/2003 | Hirayama | |
| 2003/0213150 A1 | 11/2003 | Caeran | |
| 2003/0233770 A1 | 12/2003 | Foscaro | |
| 2004/0019309 A1 | 1/2004 | Nelson et al. | |
| 2004/0049951 A1 | 3/2004 | Chen | |
| 2004/0084390 A1 * | 5/2004 | Bernstein | F25D 25/02 211/59.2 |
| 2004/0111049 A1 | 6/2004 | Nelson | |
| 2004/0167453 A1 | 8/2004 | Peters | |
| 2004/0172854 A1 | 9/2004 | Delgorgue et al. | |
| 2004/0236259 A1 | 11/2004 | Pressman et al. | |
| 2004/0250452 A1 | 12/2004 | Farys | |
| 2005/0070833 A1 | 3/2005 | Shields | |
| 2005/0085755 A1 * | 4/2005 | Rabe | A61F 5/0111 602/27 |
| 2005/0171461 A1 | 8/2005 | Pick | |
| 2005/0177083 A1 | 8/2005 | Heil | |
| 2005/0178028 A1 | 8/2005 | Light | |
| 2005/0204585 A1 | 9/2005 | Loveridge et al. | |
| 2005/0217147 A1 | 10/2005 | Dion | |
| 2005/0222531 A1 | 10/2005 | Moore | |
| 2005/0236784 A1 | 10/2005 | Zampieri et al. | |
| 2006/0005432 A1 | 1/2006 | Kassai et al. | |
| 2006/0032090 A1 | 2/2006 | Chen et al. | |
| 2006/0059719 A1 | 3/2006 | Lebo | |
| 2006/0084899 A1 * | 4/2006 | Verkade | A61F 5/0127 602/27 |
| 2007/0027420 A1 | 2/2007 | Yu | |
| 2007/0049855 A1 | 3/2007 | Mattear | |
| 2007/0056189 A1 | 3/2007 | Schafer Mathison | |
| 2007/0113427 A1 | 5/2007 | Mansfield | |
| 2008/0010860 A1 | 1/2008 | Gyr | |
| 2008/0120871 A1 | 5/2008 | Sato et al. | |
| 2008/0263897 A1 | 10/2008 | Shepherd et al. | |
| 2009/0031585 A1 | 2/2009 | Shepherd et al. | |
| 2009/0044427 A1 | 2/2009 | Shepherd et al. | |
| 2009/0084390 A1 | 4/2009 | Davis et al. | |
| 2009/0105704 A1 * | 4/2009 | Gordon, Jr. | A61F 13/066 606/27 |
| 2009/0165333 A1 | 7/2009 | Litchfield et al. | |
| 2009/0216167 A1 | 8/2009 | Harris | |
| 2009/0247920 A1 | 10/2009 | Clements et al. | |
| 2010/0011620 A1 | 1/2010 | Nakano | |
| 2010/0137770 A1 | 6/2010 | Ingimundarson et al. | |
| 2011/0028877 A1 | 2/2011 | Vollbrecht et al. | |
| 2011/0035967 A1 | 2/2011 | Shmueli | |
| 2011/0179673 A1 | 7/2011 | Bisson et al. | |
| 2014/0230278 A1 | 8/2014 | Schafer Mathison | |
| 2015/0216702 A1 | 8/2015 | Best et al. | |
| 2015/0265449 A1 | 9/2015 | Togninalli et al. | |
| 2015/0374527 A1 | 12/2015 | Wenger | |
| 2016/0030222 A1 | 2/2016 | Collier et al. | |
| 2016/0157551 A1 | 6/2016 | Goldberg | |
| 2018/0042751 A1 | 2/2018 | Derose | |
| 2018/0235312 A1 | 8/2018 | Hanft | |

FOREIGN PATENT DOCUMENTS

| | | | |
|---|---|---|---|
| EP | 0416913 A2 | 3/1991 | |
| EP | 0744906 A1 | 12/1996 | |
| EP | 1152720 A1 | 11/2001 | |
| EP | 1234560 A1 | 8/2002 | |
| EP | 1346710 A1 | 9/2003 | |
| EP | 1928369 A2 | 6/2008 | |
| EP | 2050429 A1 | 4/2009 | |
| EP | 2379020 A1 | 10/2011 | |
| WO | 91/12781 A1 | 9/1991 | |
| WO | 95/22264 A1 | 8/1995 | |
| WO | 97/36507 A1 | 10/1997 | |
| WO | 00/40202 A2 | 7/2000 | |
| WO | 00/48537 A1 | 8/2000 | |
| WO | 2004/009001 A1 | 1/2004 | |
| WO | 2004/098467 A1 | 11/2004 | |
| WO | 2004/108026 A1 | 12/2004 | |
| WO | 2006/061603 A2 | 6/2006 | |

(56) References Cited

FOREIGN PATENT DOCUMENTS

| WO | 2007/041345 A2 | 4/2007 |
| WO | 2007/078845 A2 | 7/2007 |
| WO | 2008/028643 A1 | 3/2008 |
| WO | 2009/023094 A2 | 2/2009 |
| WO | 2009/090259 A1 | 7/2009 |
| WO | 2010/065097 A1 | 6/2010 |
| WO | 2014/043695 A1 | 3/2014 |
| WO | 2017/209770 A1 | 12/2017 |
| WO | 2020/069149 A1 | 4/2020 |
| WO | 2020/069151 A1 | 4/2020 |

OTHER PUBLICATIONS

International Preliminary Report on Patentability received for PCT Patent Application No. PCT/US2016/035853, dated Dec. 13, 2018, 11 pages.

International Search Report and Written Opinion received for PCT Patent Application No. PCT/US2013/060152, dated Jan. 3, 2014, 8 pages.

International Search Report and Written Opinion received for PCT Patent Application No. PCT/US2016/035853, dated Mar. 21, 2017, 15 pages.

International Search Report and Written Opinion received for PCT Patent Application No. PCT/US2019/053182, dated Feb. 20, 2020, 15 pages.

International Search Report and Written Opinion received for PCT Patent Application No. PCT/US2019/053185, dated Feb. 4, 2020, 14 pages.

Partial Supplementary European Search Report issued in EP Application No. EP13837423.6, dated Apr. 21, 2016, 7 pages.

Supplemental EP Search Report issued in EP Application No. 13837423.6 dated Jul. 28, 2016, 11 pages.

* cited by examiner

ANKLE BRACE DEVICES, SYSTEMS AND METHODS

CROSS-REFERENCE TO RELATED APPLICATION

This application is a continuation of International Application No. PCT/US2016/035853, with an international filing date of Jun. 3, 2016, which is incorporated by reference herein in its entirety.

TECHNICAL FIELD

This disclosure relates generally to protective and supportive athletic gear and methods of making the same. The instant disclosure relates to devices and methods of supporting a user's ankle, such as ankle straps and ankle braces. More particularly, this disclosure relates to an ankle support wearable alone or inside a shoe.

BACKGROUND

Each year, many people, both athletes and non-athletes, suffer ankle injuries. In some cases, athletes wrap their ankles with adhesive tape in an attempt to prevent ankle injuries and/or to support their ankles after an injury has occurred. In many instances, athletes and others use ankle braces to protect and/or to rehabilitate their ankles.

Devices for supporting or stabilizing the foot or ankle of a wearer may be worn by a user for everyday use and/or for use when engaging in physical activity. Injuries to the foot or ankle are common and may affect a user's physical ability and/or athletic performance. For certain users it may be beneficial to use an artificial structure to support a foot or ankle that has been weakened or injured. Certain rigid structures may be worn through the day and/or when engaging in sports to provide structural support, or prevent further injury. Often a physician or healthcare worker may apply a custom fitted support or structure to the outside of user's limb to provide weight bearing support to the user's limb.

While a variety of ankle braces are known, there is a desire for continued improvement in the performance and comfort of known ankle braces. Certain support structures for the foot or ankle of a user, such as straps or braces, are available and may provide certain advantages such as agility, comfort, or weight bearing capabilities. However, certain options may be unsuitable because of particular characteristics. For example, sleeves that are currently available may be flexible or comfortable, but may not provide adequate support. In other instances, a custom fitted device may be costly and/or require extensive customization for a user. Additionally, certain devices that provide structural support may be uncomfortable, or unsuited for use in certain sports that require a particular level of agility or movement by the user's limbs. There is thus a need for a device or method for supporting a limb or limbs of a user that provides suitable weight bearing capability yet is flexible and comfortable enough to be used during sports and is also cost effective and accessible.

SUMMARY

Disclosed herein is an ankle brace comprising an ankle wrap assembly including a main body having an inner surface, an outer surface, a top, a bottom, a front defining a foot opening, a first side panel, a second side panel, a rear, and a bottom panel. The ankle brace includes first and second ankle pads attached to the main body; a first support attached to the main body first side panel, and a second attached to the main body second side panel, and a bottom support. The ankle brace is configured to be secured to a user's ankle when worn.

Also disclosed herein is an ankle brace system comprising an ankle wrap assembly configured to receive the ankle of a user, and including a main body having an inner surface, an outer surface, a top, a bottom, a front defining a forefoot sleeve, a lateral side panel, a medial side panel, a rear defining a rear opening, and a bottom panel. The ankle brace system also at least one of first and second ankle pads on the ankle wrap inner surface; first and second internal supports; a bottom support; and first and second external supports. The ankle brace system also includes a strap system including a lower rear strap, an upper rear strap, a first cross strap, a second cross strap, and an ankle strap.

Also disclosed herein is an ankle support system comprising a harness assembly configured to receive an ankle and a portion of a foot of a user, the harness including an outer surface, and inner surface, a front defining a foot sleeve, a lateral panel, a medial panel, a rear portion defining an opening to receive the foot of a user, a top defining an ankle sleeve, and a bottom panel. The ankle support system also includes a medial malleolus pad and a lateral malleolus pad attached to the inner surface of the main body. The ankle brace system also includes an internal support assembly including a lateral support plate having a top and bottom, a medial support plate having a top and bottom, and a bottom support configured to extend along the bottom panel, and having a first end overlapping the lateral support plate bottom, and a second end overlapping the lateral support plate bottom. The ankle brace system also includes a strap assembly including a first and second cross strap, a first and second rear strap, and an ankle strap.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

In some embodiments, the instant disclosure includes an ankle brace or ankle brace system that may be worn alone or inside a shoe. The instant disclosure includes an ankle brace system having various structures that provide support to a user's ankle when worn. Though ankle braces or ankle brace systems according to various embodiments include the features and/or achieve the advantages disclosed herein, alternative or additional features and advantages are contemplated. In some embodiments, an ankle brace system forms a hybrid support brace design having features of both an ankle sleeve and an ankle brace.

Figure 1A:
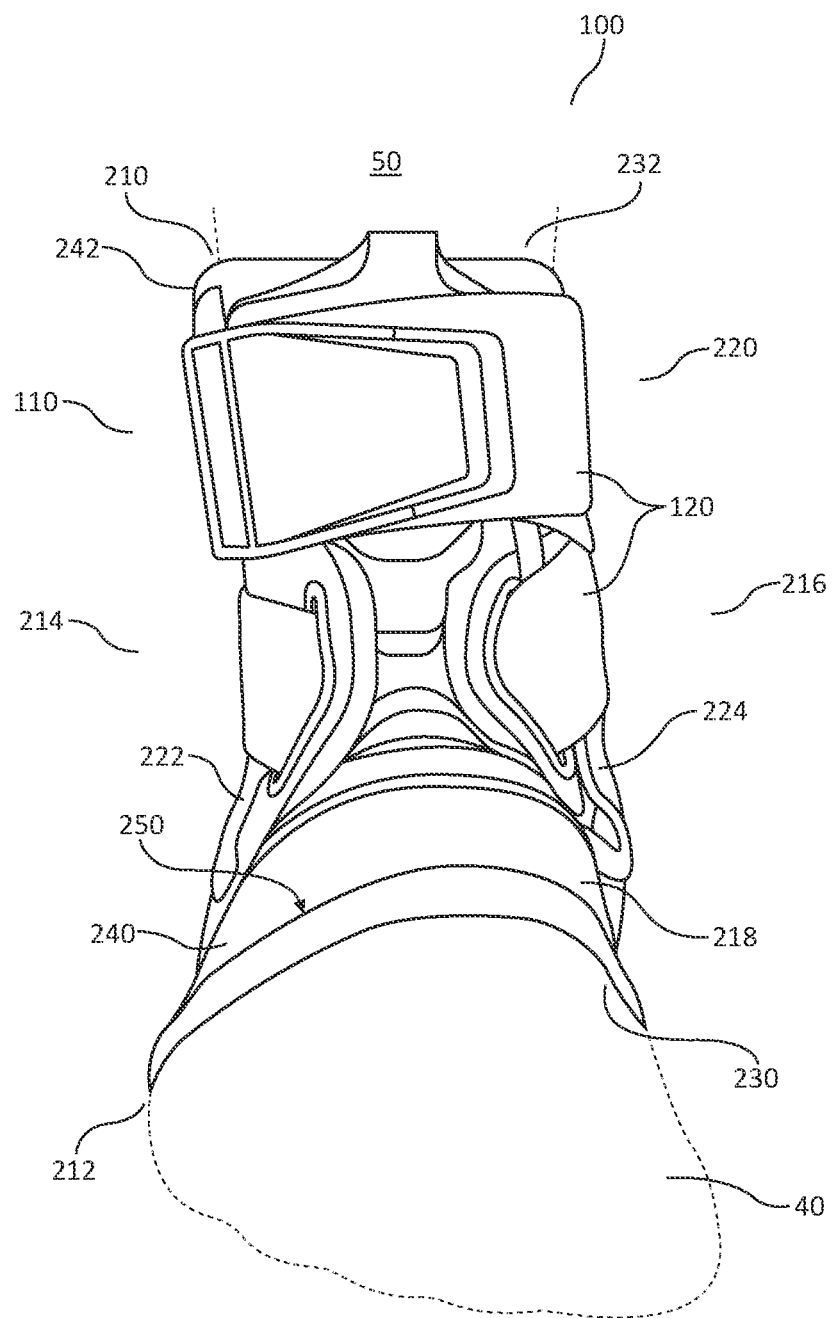
FIG. 1A is a front view of an embodiment of an ankle brace.
Figure 1B:
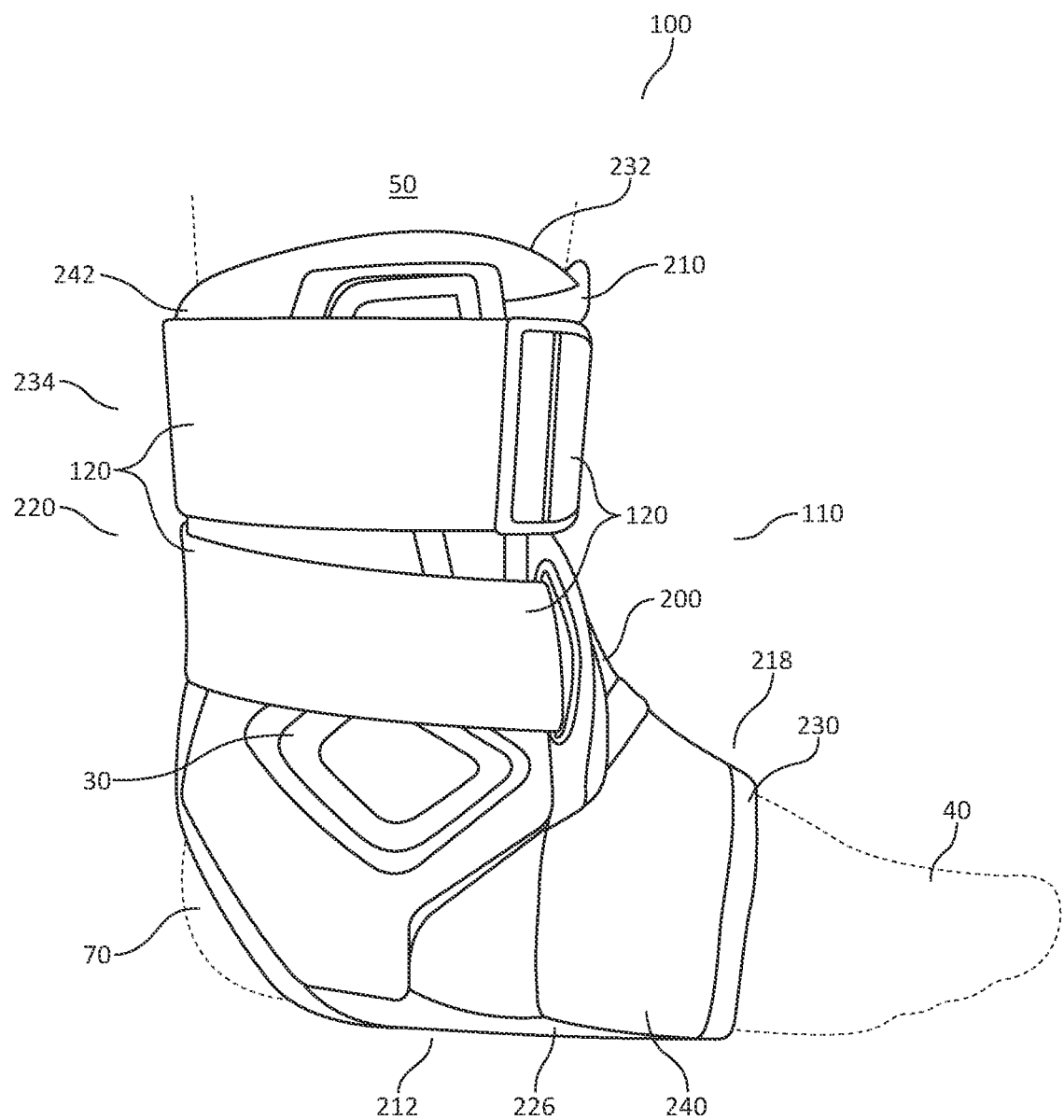
FIG. 1B is a side view of an embodiment of an ankle brace.

FIGS. 1A-1B provide a view of the ankle brace system 100 on a wearer's foot 40 from various angles to illustrate certain features. As shown in FIGS. 1A-1B an ankle brace system 100 may include an ankle wrap assembly 110 that may be used as a harness for a user's foot when worn, and a strap assembly 120.

As shown in FIGS. 1A-1B, in some embodiments, the ankle wrap assembly 110 includes a main body 200. The main body 200 has a top 210, a bottom 212, a first side 214, and a second side 216. The main body 200 has a front 218 and a rear 220. In some embodiments, the first side 214 is located on the lateral side of a user's foot 40 and/or ankle 30 when worn. In some embodiments, the second side 216 is located on the medial side of a user's foot 40 and/or ankle 30 when worn.

As used herein, "medial" refers generally to a location toward the middle, midline, or median plane of a user's body. As used herein, "lateral" refers generally to a location toward the side or outside of a user's body. That is the medial side of a user's foot is the side that faces inward, generally toward the center of the body, i.e. toward the opposing leg. The lateral side of a user's foot is the side that faces outward, generally from the user's body, i.e. away from the opposing foot. Thus the medial side of a user's right foot is on the left side of the right foot, and the lateral side of a user's right foot is on the right side of the right foot. The medial side of a user's left foot is on the right side of the foot, and the lateral side of a user's left foot is on the left side of the foot.

In some embodiments, the ankle wrap assembly 110 is configured to receive an ankle 30 and a portion of a foot 40 of a user. In some embodiments, the ankle wrap assembly 110 is sized to receive an ankle 30 and a portion of a leg 50 of a user. In some embodiments, the front 218 of the main body 200 defines a front opening 230. The top 210 of the main body 200 may define a top opening 232. The rear 220 may define a rear opening 234. In some embodiments, the front 218 of the main body 200 defines a foot sleeve 240, and the top 210 of the main body 200 defines a leg sleeve 242. In some embodiments, the rear opening 234 defines an opening sized to be suitable for receiving a foot 40 and/or ankle 30 of a user.

In some embodiments, the main body first side 214 is formed from a first side panel 222, and the main body second side 216 is formed from a second side panel 224. In some embodiments the bottom 212 is formed from a bottom panel 226. In some embodiments, the first side panel 222 defines a lateral side panel, described further below. In some embodiments the second side panel 224 defines a medial side panel. In some embodiments, the main body 200 defines an outer surface 250 and an inner surface 252 (described further below). The main body 200 may be formed from material that is resilient yet elastic to support a user's ankle 30 or foot 40 and allow a user to move without restraint.

Figure 2:
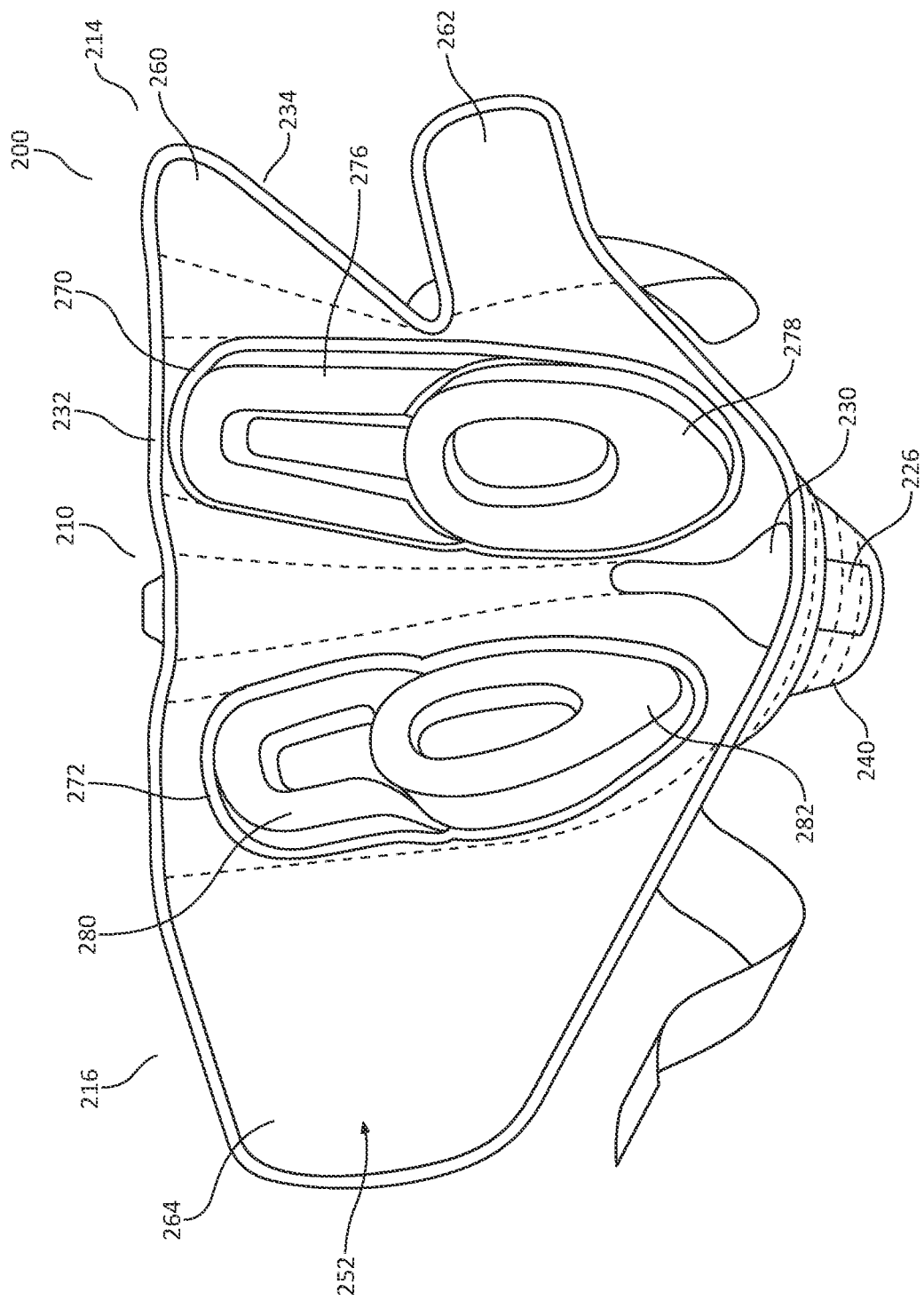
FIG. 2 is a rear view of an embodiment of an ankle brace, showing an inside.

FIG. 2 is a rear view of the main body 200 shown with the rear opening 234 open to illustrate certain features. As shown in FIG. 2, the rear 220 of the main body 200 may define a rear opening 234. As shown in FIG. 2, the front 218 defines a front opening 230 and a foot sleeve 240. The top 210 of the main body 200 defines the top opening 232. In some embodiments, the rear opening 234 may be connected with the top opening 232. In some embodiments, the rear opening 234 may be formed separate from the top opening 232.

As shown in FIG. 2, the main body 200 may include a top rear strap 260 and a bottom rear strap 262. The top and bottom rear straps 260, 262 may be on either the lateral or medial side of a main body 200. That is, the top and bottom rear straps 260, 262 may be located on either the first or second side 214, 216 of the main body 200. The rear opening 234 may be closed by connecting the top rear strap 260 and/or the bottom rear strap 262 with a location on the opposite side of the main body 200. As shown in FIG. 2, the main body 200 may include a rear panel 264. The rear opening 234 may be closed by attaching the top rear strap 260 and/or the bottom rear strap 262 with the rear panel 264. The top and bottom rear straps 260, 262 may be attached to the rear panel 264 by any suitable attachment mechanism such as a clasp, a clamp, or a hook and loop material such as Velcro®. The rear opening 234 and foot sleeve 240 may form a quick-wrap closure that is easy to wear and provides a personalized volume fit.

As shown in FIG. 2, in some embodiments the inner surface 252 of the main body 200 includes a first pad 270 and a second pad 272. The first and second pads 270, 272 may be suitably shaped ankle pads attached to the ankle wrap inner surface 252. In some embodiments, the first and second pads 270, 272 may be shaped to receive an ankle or ankle bone of a user. For example, a first pad 270 may have a top and bottom portion 276, 278, and the second 272 pad may have a top and bottom portion 280, 282. The first pad top and bottom portion 276, 278 and the second pad top and bottom portion 280, 282 may be shaped to receive part of a user's ankle, such as a medial malleolus or a lateral malleolus when worn. For example, in some embodiments, the first pad top and bottom portion 276, 278 form a lateral malleolus pad and the second pad top and bottom portion 280, 282 form a medial malleolus pad. In some embodiments, the first and second ankle pads 270, 272 are shaped to conform to the outer surface of a user's ankle adjacent the lateral and medial malleolus bones.

Figure 3:
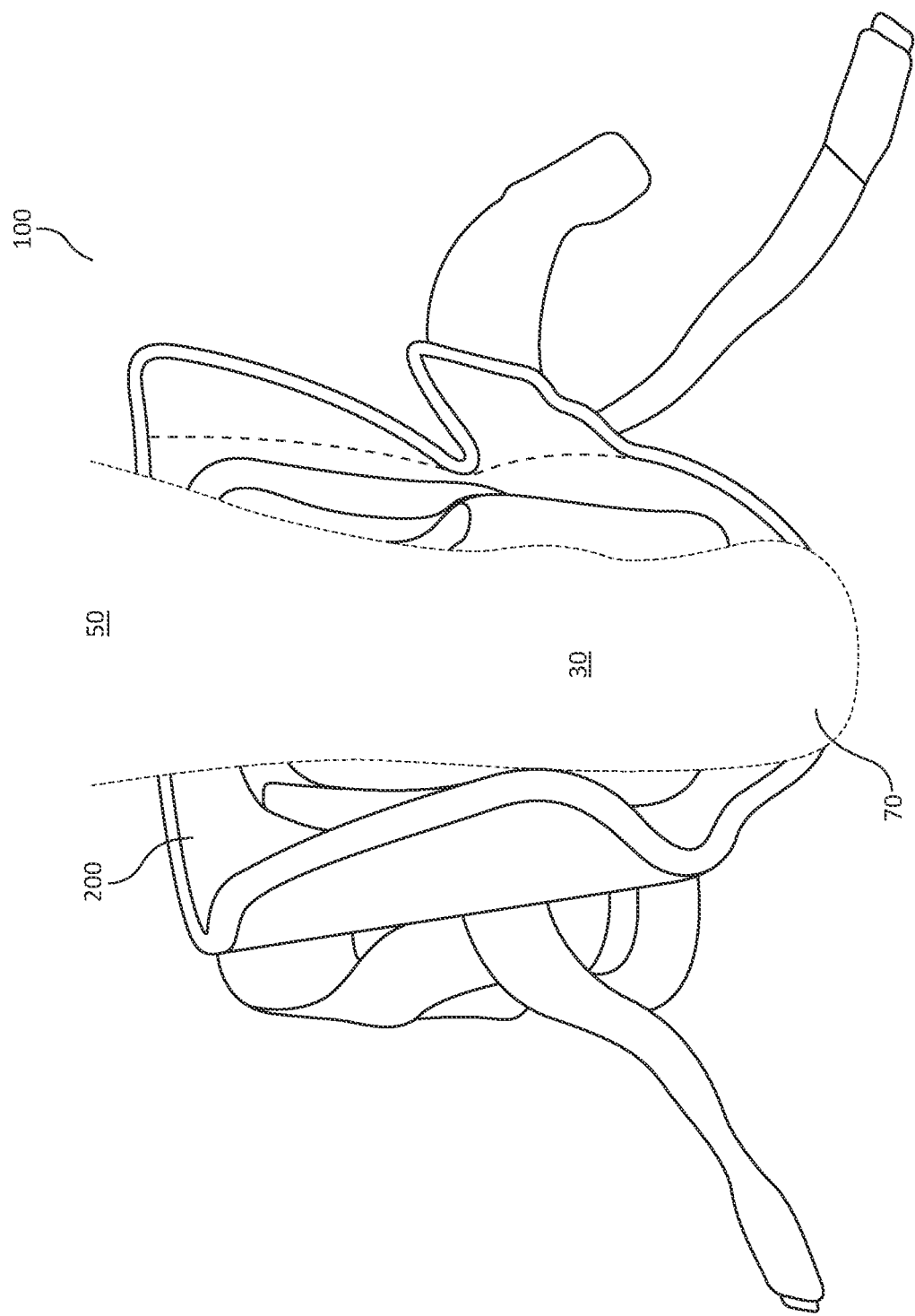
FIG. 3 is a rear view of an embodiment of an ankle brace, showing a user's ankle.

FIG. 3 shows a user's ankle 30, heel 70 and part of a user's leg 50 received in the main body 200 to illustrate a possible orientation for the ankle brace system 100 when worn by a user. The main body 200 is shaped to receive at least a portion of a user's ankle 30 when worn. As shown in FIG. 3, the main body 200 may be suitably shaped to receive a user's right foot (hidden from view) and/or ankle 30 when worn. In some embodiments, the main body 200 may be a mirror image of the embodiment shown in FIG. 3, and suitably shaped to receive a user's left foot and/or ankle when worn.

Figure 4:
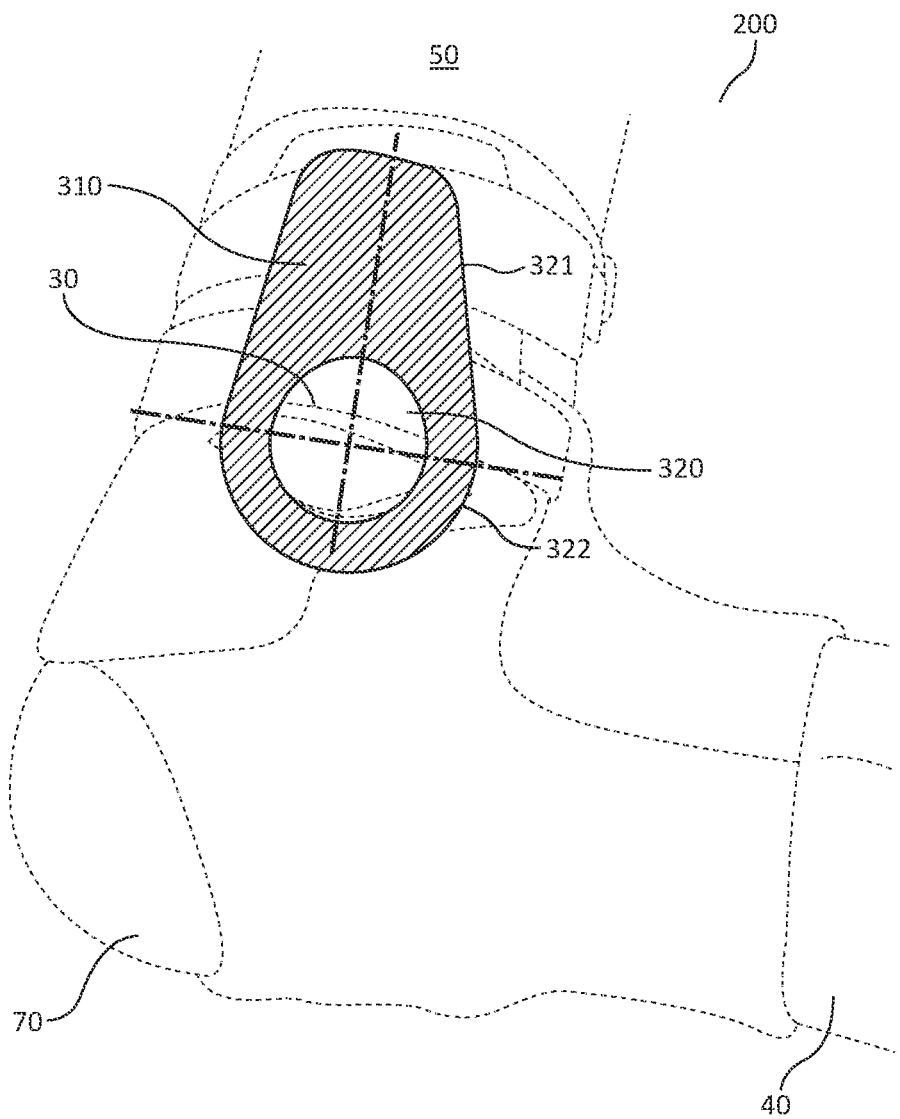
FIG. 4 is schematic view of an embodiment of an ankle brace, showing an internal support.

FIG. 4 is a perspective view of the ankle brace system 100 showing internal components highlighted by pattern. The patterned components are shown to illustrate features that may be located underneath or within the main body 200, and may be hidden from view from an outside perspective of the main body 200. As shown in FIG. 4, the main body 200 may include a first internal support 310 within the main body first side panel 222. The main body 200 may also include a second internal support 312 (hidden from view) within the main body second side panel 224. It is also envisioned that certain embodiments of a main body 200 may be formed without these additional features. That is the main body 200 may be formed with an alternative configuration without the first and second internal supports 310, 312.

The first and second internal supports 310, 312 may be shaped to conform to the outside of a user's leg 50 and/or ankle 30 and may define an opening 320 for receiving an ankle bone of a user. In certain embodiments, the first internal support 310 may be fixed to the main body 200 by an upper portion 321 of the first internal support 310. In some embodiments, the first internal support may also have a lower portion 322 that is not fixed to the main body 200. That is, the lower portion 322 of the first internal support 310 may be floating or not directly attached to the main body. Similar configurations of an upper portion 321 being fixed and a lower portion 322 having a floating or suspended configuration that is not directly attached to the main body may be used for the second internal support 312.

Figure 5C:
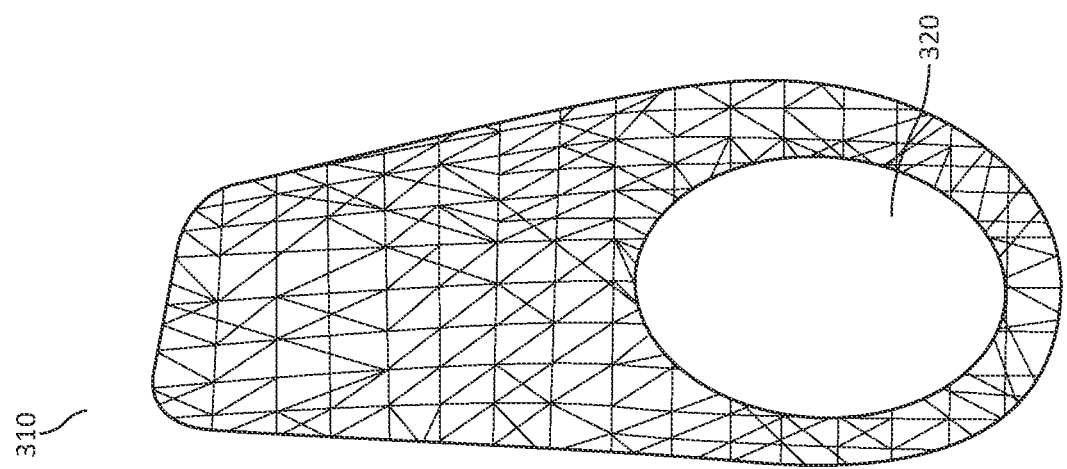
FIGS. 5A-5C are schematic views of embodiments of internal supports that may be used with an ankle brace.
Figure 5B:
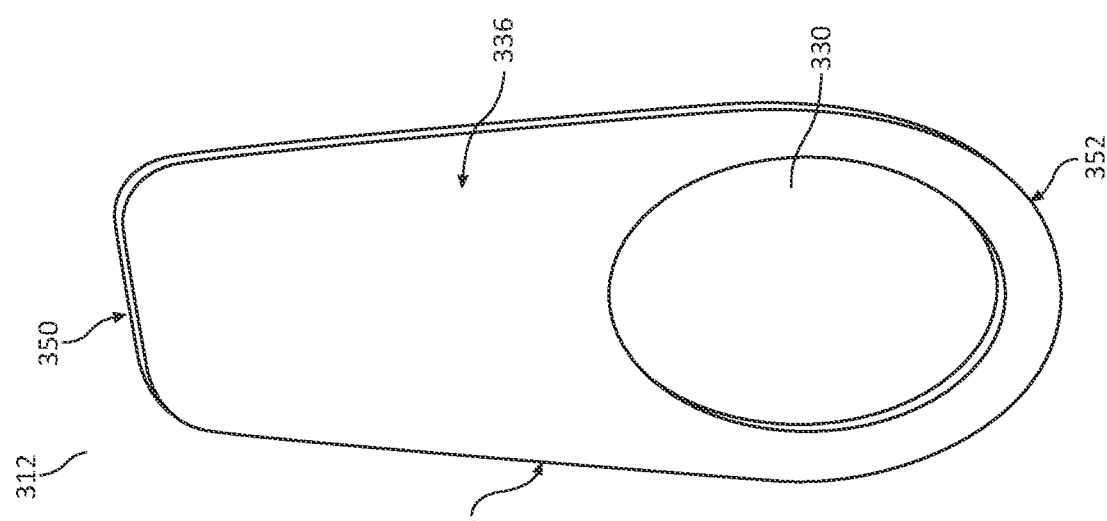
Figure 5A:
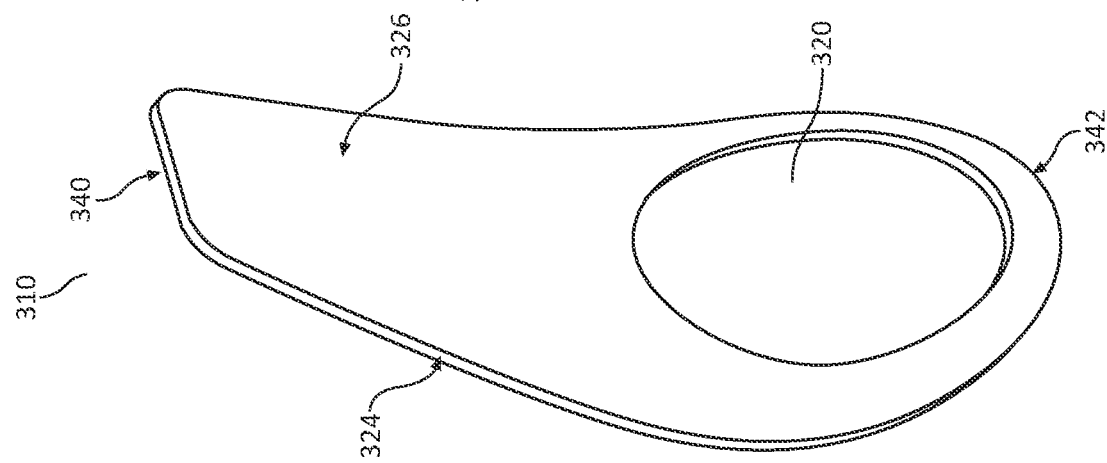

FIGS. 5A-5B show the first and second internal support 310, 312 from a perspective view. FIG. 5C shows the first internal support 310 from an alternative angle to show an overall profile. As shown in FIGS. 5A-5B, in some embodiments, the first and second internal supports 310, 312 are comprised of planar structures having a first surface 324, 334, a second surface 326, 336, and an opening 320, 330. The first and second internal supports 310, 312 may each have a top edge 340, 350 and a bottom edge 342, 352. In some embodiments, the first and second internal supports 310, 312 comprise rigid support shells molded to conform to the lateral and medial sides of a user's ankle. In some embodiments, each of the first and second internal supports 310, 312 define an opening 320, 330 suitable for receiving a user's medial or lateral malleolus. In some embodiments, the first and second internal supports 310, 312 may be lateral and medial ergonomically contoured molded support stays configured to surround the sides of a user's ankle and extend above and below the ankle joint.

In some embodiments, the first and second internal supports 310, 312 comprise lateral and medal support plates that are shaped to conform to the outer surface of a user's ankle adjacent the lateral and medial malleolus bones. In some embodiments, the lateral plate defines an opening 320 shaped to cradle a user's lateral malleolus bone and the medial plate defines an opening 330 shaped to cradle a user's medial malleolus bone. The first and second internal supports 310, 312 may also be referred to as a lateral ankle stay, and a medial ankle stay respectively. The first and second internal supports 310, 312 may be formed from a rigid material such as plastic or a composite material. The first and second internal supports 310, 312 may be formed from material that is load bearing, yet also flexible in order to move with a user's body. The first and second internal supports 310, 312 may be formed by any suitable process such as die cutting or injection molding material into a suitable size and shape for the side of a user's ankle.

Figure 6:
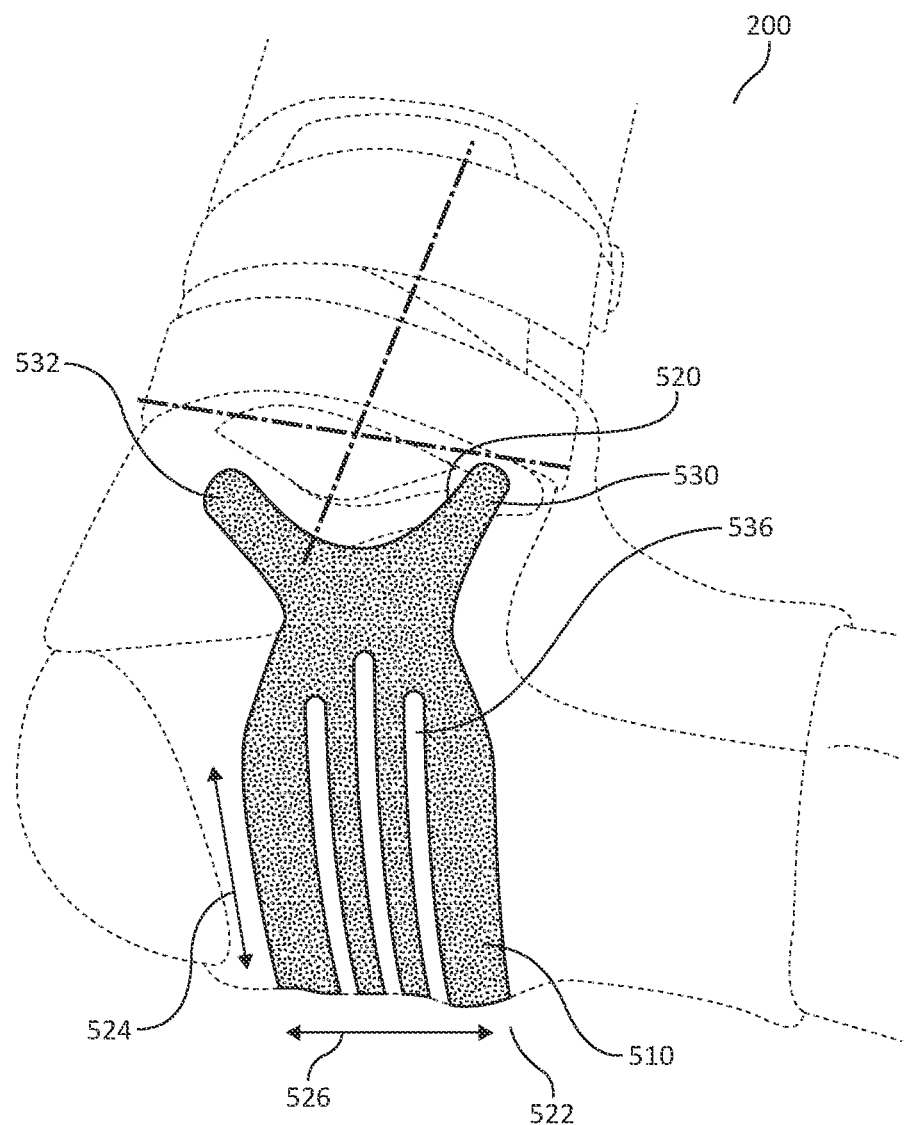
FIG. 6 is a schematic view of an embodiment of an ankle brace, showing a bottom support.

FIG. 6 is a perspective view of a bottom support 510. As shown in FIG. 6, the bottom support has a first end 520, a second end 522 (hidden from view), and a length in between 524. The bottom support 510 also has a width 526. In some embodiments, the bottom support first end 520 has a first prong 530 and a second prong 532. In some embodiments, the bottom support second end 522 has a matching size and shape to the first end 520. The bottom support 510 may include openings or slats 536 along the length 524 of the bottom support 510. The bottom support 510 may have multiple openings 536 along the width of the bottom support 510. The openings 536 may allow for added flexibility or ventilation when the main body 200 is worn.

In some embodiments, the bottom support 510 may be shaped as a stirrup. In some embodiments, the bottom support 510 may be shaped as a stirrup stay configured to wrap under a user's foot when worn. As shown in FIG. 6, the bottom support first end 520 may be located adjacent a lateral side of a user's ankle, the length 524 may extend under a user's foot, and the second end 522 may be located adjacent a medial side of the user's ankle. The bottom support 510 may be formed using any suitable process such as die cutting or injection molding material such as plastic or a composite material. The bottom support 510 may be formed from material that is load bearing, yet also flexible in order to move with a user's body when worn.

Figure 7:
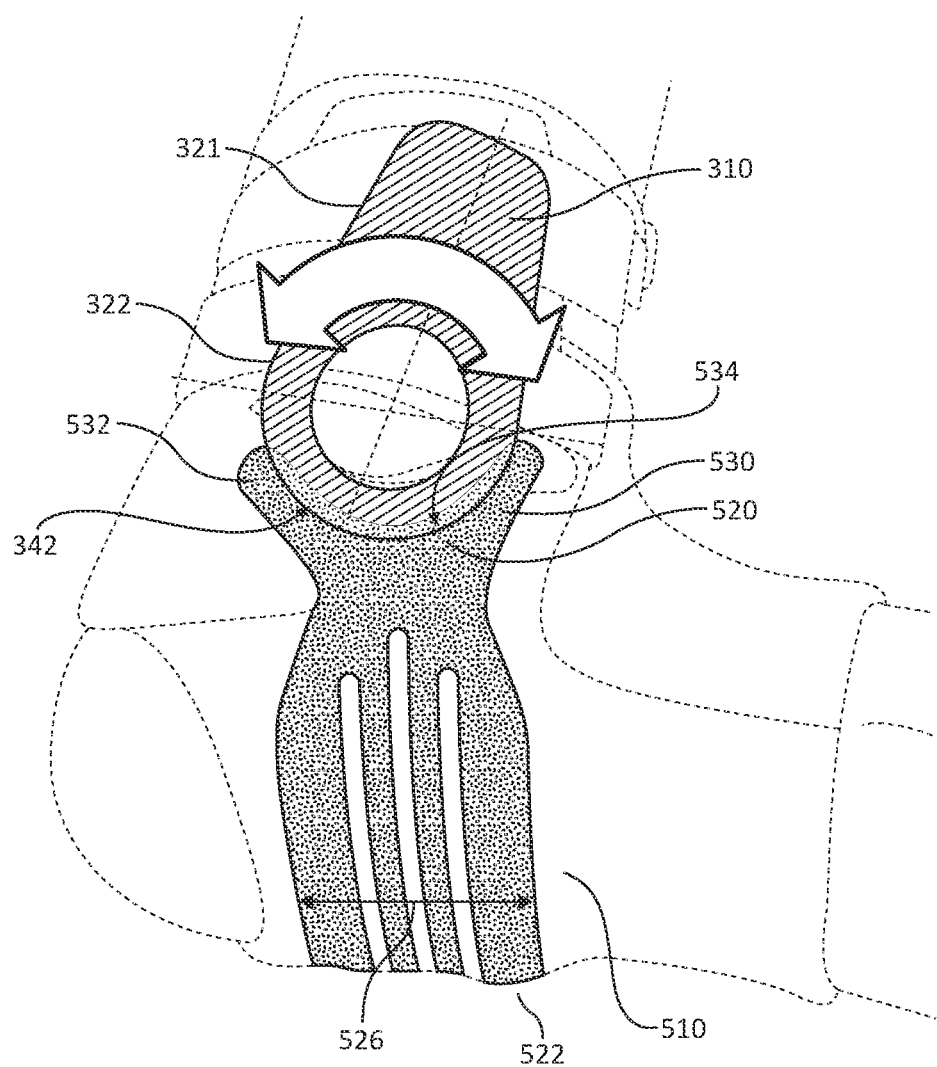
FIG. 7 is a schematic view of an embodiment of an ankle brace, showing an internal support and a bottom support.

As shown in FIG. 7, the bottom support first end 520 may be configured to interact with the first internal support 310 and the bottom support second end 522 is configured to interact with the second internal support 312 (hidden from view). In some embodiments, the bottom support first end 520 may be configured to overlap with the first internal support 310 and the bottom support second end 522 is configured to overlap with the second internal support 312 (hidden from view). The bottom support 510 may be an articulating stirrup configured to extend under the foot and wrap up the sides adjacent to the lower area of a user's lateral and medial ankle joint.

As shown in FIG. 7, the bottom support 510 may by shaped to conform to the first and second internal supports 310, 312 and form a complementary fit. For example, the bottom support first end 520 may have first and second prongs 530, 532 shaped along the width 526 of the bottom support 510. In some embodiments, the first and second prongs 530, 532 may define a first edge 534. In some embodiments, the second internal support 312 may have first and second prongs defining a second edge (hidden from view). The bottom support first edge 534 may be configured to interact with the first internal support bottom edge 342. The bottom support first edge 534 and first and second prongs 530, 532 may be configured to cradle or hold the first internal support 510 along the bottom edge 342.

In some embodiments, the bottom support second end 522 may have a similar structure and be configured to hold the second internal support 512 along the bottom edge (hidden from view). In some embodiments, the bottom support first and second ends 520, 522 are shaped to receive the first and second internal supports 310, 312 in a conforming fit that allows the first and second internal supports 310, 312 to move with a user's leg or ankle in the direction of the arrows, while the bottom support 510 remains in place with the bottom of the user's foot.

In some embodiments, the first internal support lower portion 322 and second internal support lower portion (hidden from view) may be configured to be not directly attached to the main body 200. For example, the first internal support lower portion 322 and second internal support lower portion (hidden from view) may be floating or suspended relative to the main body 200 to allow for a hinging aspect in relation to the bottom support 510. In some embodiments, the bottom support first and second ends 520, 522 are shaped to receive the first and second internal supports 310, 312 and allow the first and second internal supports 310, 312 to rotate in the direction of the arrows, while the bottom support 510 remains in alignment with the sole of a user's foot. The bottom support 510 may be shaped to integrate with the first and second internal supports 310, 312 with a complementary fit. In certain embodiments, the first and second internal supports 310, 312 and the bottom support 510 are integrated to provide a support to a user's ankle, while allowing the user's leg, foot, or ankle to bend and flex without inhibiting the support. The integration of first and second internal supports 310, 312 and the bottom support 510 with overlaid components provides an integrated support design, without a mechanical hinge, or a stiff or restrictive feeling.

Figure 8:
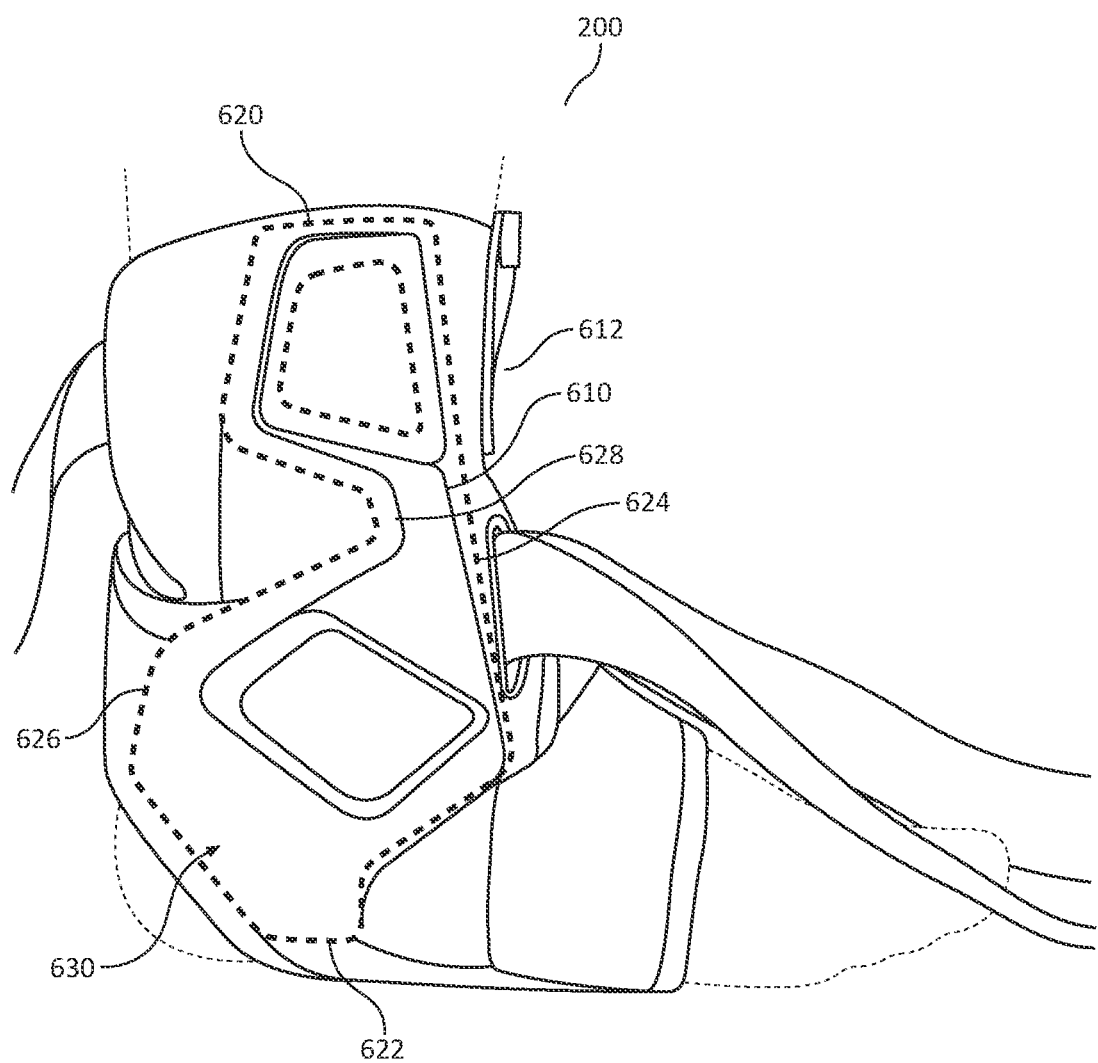
FIG. 8 is a side view of an embodiment of an ankle brace, showing an external support.

FIG. 8 is a side view of the main body 200 showing additional features that may optionally be included with certain embodiments. It is also envisioned that certain embodiments of a main body 200 may be formed without these additional features. As shown in FIG. 8, in some embodiments, the main body 200 may include a first external support 610. In some embodiments, the main body 200 may also include a second external support 612 (hidden from view). Reference is made to describe the first external support 610; however, similar descriptions may apply to the second external support 612 (shown below in FIG. 10). As shown in FIG. 8, the first external support 610 may be a relatively planar structure having a top edge 620, a bottom edge 622, a front edge 624, and a rear edge 626. In some embodiments, the first external support may include a break 628 along the rear edge 626. The first external support 610 may have an inner surface attached to the wrap assembly main body 200 and an outer surface 630 facing away from the main body 200. In some embodiments, the first external support 610 may be configured to conform to the lateral side of a user's foot and/or ankle, and the second external support 612 may be configured to conform to the medial side of a user's foot and/or ankle. In some embodiments, the first external support 610 may be configured as a lateral external support and the second external support 612 may be configured as a medial external support.

In some embodiments, the first and second external supports 610, 612 may include rigid support plates shaped to conform to the lateral and medial sides of a user's ankle. The first and second external supports 610, 612 may shaped to conform and be overlaid on the main body 200 over the user's foot and/or ankle and the first and second internal supports 310, 312 shown in FIG. 7. The first and second external supports 610, 612 may be external support assemblies including a lateral support and a medial support. The first and second external supports 610, 612 may be formed from a rigid material such as plastic or a composite material. The first and second external supports 610, 612 may be formed from material that is load bearing yet also flexible in order to move with a user's body when worn. In some embodiments, the first and second external supports 610, 612 may be formed using any suitable method such as die cutting or injection molding from thermoplastic material that may be molded to form an anatomically wrapping contour fit.

Figure 9:
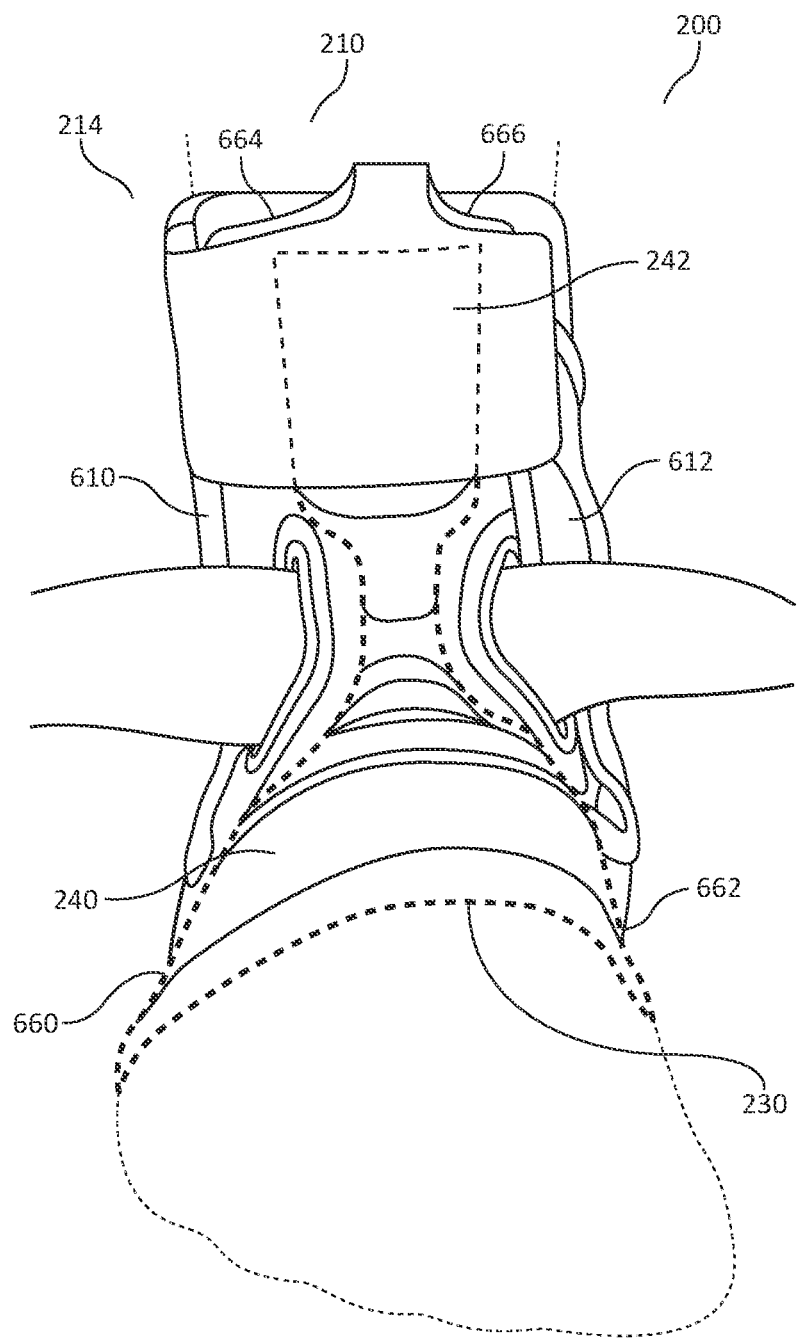
FIG. 9 is a front view of an embodiment of an ankle brace, showing an external structure.
Figure 10:
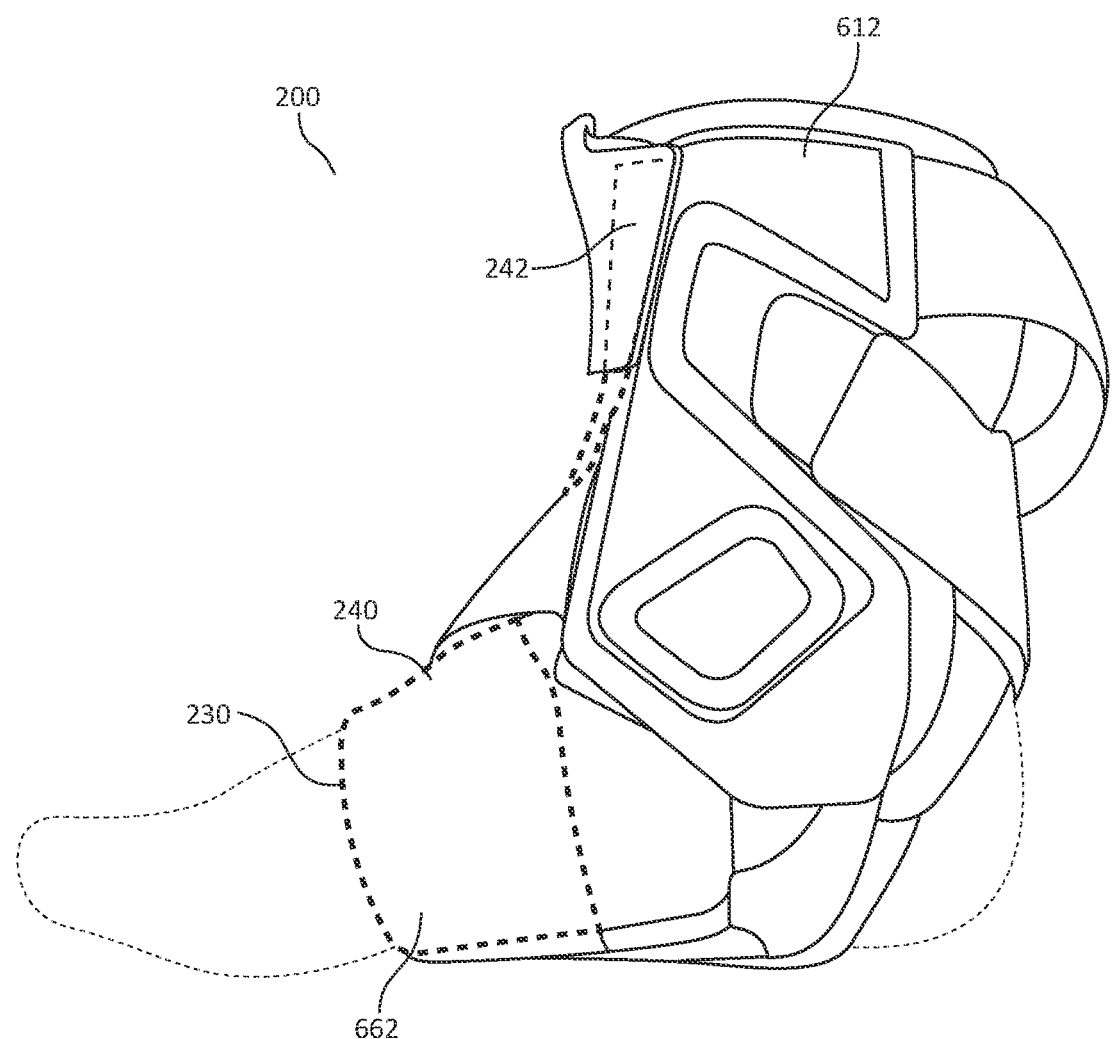
FIG. 10 is a side view of an embodiment of an ankle brace, showing an external structure.

FIG. 9 is a front view of the main body 200 showing the position of the first and second external supports 610, 612 and various features of the main body 200. As shown in FIG. 9, the first external support 610 may be located on the first side 214 of the main body 200 and the second external support 612 may be located on the second side 216 of the main body 200. As shown in FIGS. 9 and 10, the first and second external supports 610, 612 may provide a supporting structure that has minimal stretching when subjected to weight or a load bearing positon. The main body 200 may have certain portions of the foot sleeve 240 configured to stretch in response to a user's movement. For example, a first side 660 and second side 662 of the foot sleeve 240 may stretch or move with a user's body when worn for a comfortable fit between the user's foot or ankle and the main body 200 including the first and second external supports 610, 612. Additional stretch or flex areas near the top of the leg sleeve 242 or the front opening 230 of the foot sleeve may also may stretch or move with a user's body when worn for a comfortable fit between the user's foot or ankle and the main body 200. This combination of stretch and flex zones on the main body 200 and the first and second external supports 610, 612, provides an anatomical design for a comfortable, supportive fit throughout a user's range of motion and for the duration of a user's activity. The main body 200 may thus include portions of elastic or pliable flex link design wraps that contour with a user's foot or ankle joint for the ultimate personalized fit for a user. The main body 200 may also align the first and second external supports 610, 612 in an ergonomically correct position for a comfortable feeling during a flexion and/or extension ankle motion.

As shown in FIG. 9, the main body may also include colored sections 664, 666 near the top 210. For example, the leg sleeve 242 may have colored sections 664, 666 near the top of the main body 200 to assist in fixing the main body 200 to a user when worn. This is described further below.

Figure 11:
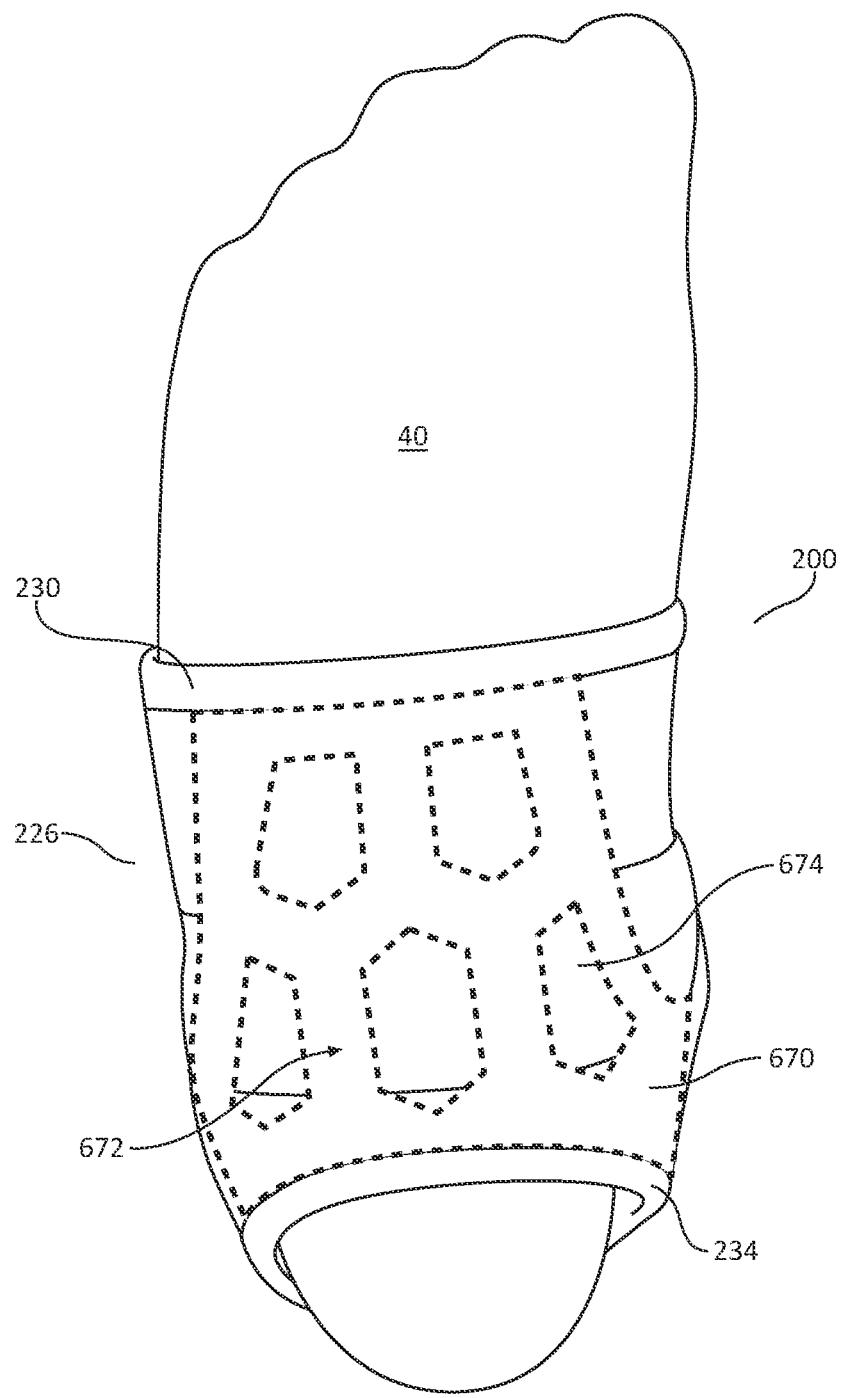
FIG. 11 is a bottom view of an embodiment of an ankle brace, showing a bottom surface.

FIG. 11 is a bottom view of the main body 200 showing the bottom panel 226. As shown in FIG. 11, in some embodiments, the bottom panel 226 may include an anti-slip layer 670 on an outer surface 672 of the bottom panel. The anti-slip layer 670 may provide greater contact stability for a user's foot 40 or heel 70 while a user is walking without wearing a shoe, or provides greater contact stability with a shoe when worn by a user. In some embodiments, the anti-slip layer 670 may be formed from a high friction material such as silicone. The anti-slip layer 670 may be bonded to the bottom panel 226 of the main body 200, or may be integrally formed with the bottom panel 226 material. The anti-slip layer 670 may be formed as a comprehensive layer, to cover the bottom panel 226. Alternatively, as shown in FIG. 11 the anti-slip layer 670 may be formed with openings 674, for example for ventilation.

Figure 12:
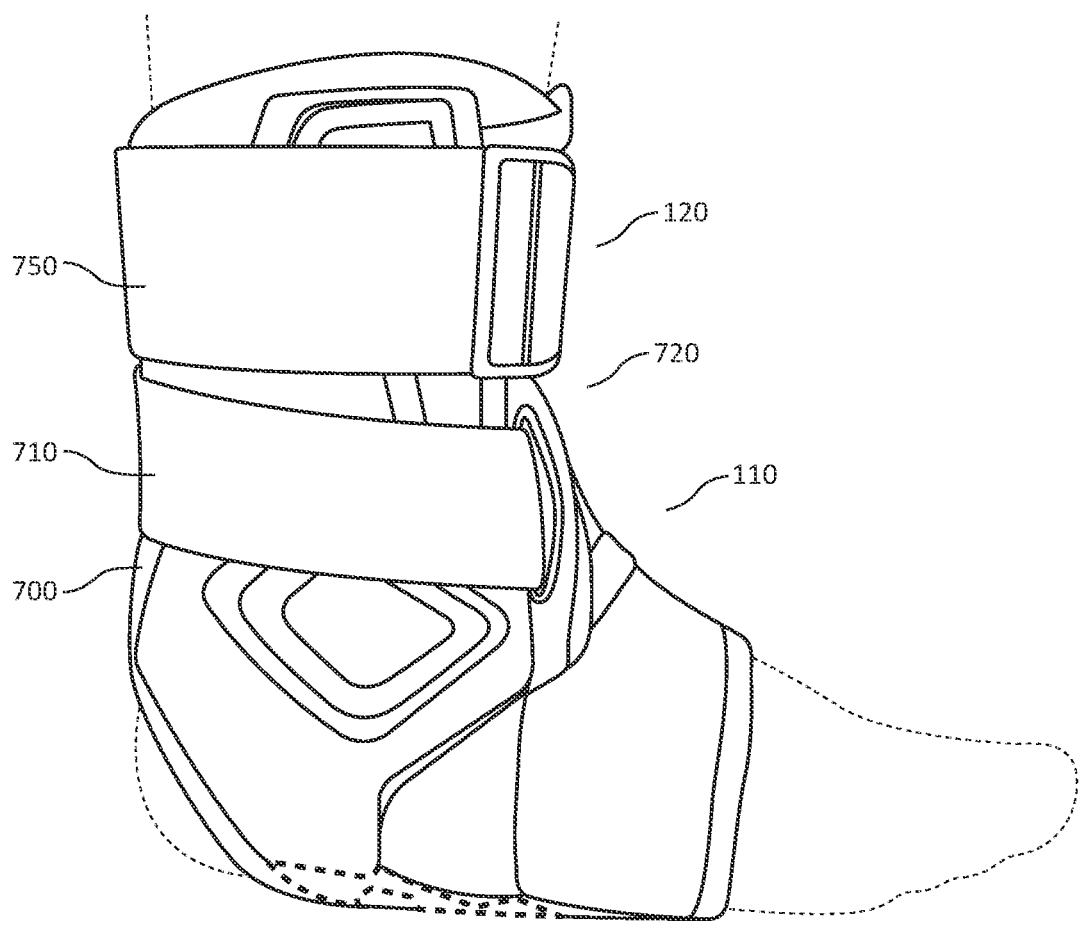
FIG. 12 is a side view of an embodiment of an ankle brace, showing a strap assembly.

FIG. 12 shows a side view of an ankle wrap assembly 110, and a strap assembly 120. In some embodiments, the strap assembly 120 may be used to maintain the wrap assembly 110 in place on a user's body when worn. In some embodiments, the strap assembly 120 may provide additional support to a user's body in addition to the wrap assembly 110. A strap assembly 120 may include a rear strap 700, a first cross strap 710, a second cross strap 720, and a top strap 750. In some embodiments, the top strap 750 may wrap around the top of a user's ankle. In some embodiments, the rear strap may include a rear top strap 260 and a rear bottom strap 262 as shown in FIG. 2.

Figure 13:
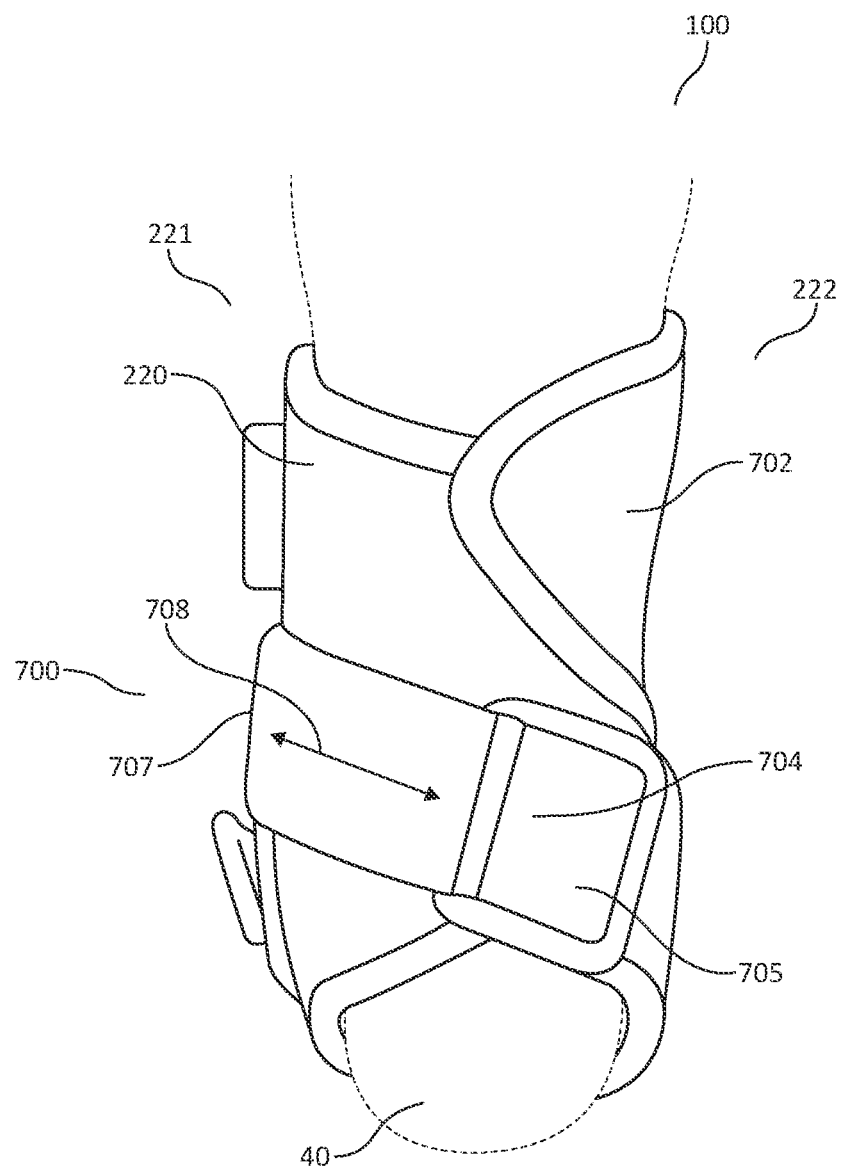
FIG. 13 is a rear view of an embodiment of an ankle brace, showing a strap assembly.

FIG. 13 is a rear view of the ankle brace system 100 showing a rear strap 700 assembly. As shown in FIG. 13, the rear strap 700 assembly may include a first rear strap 702 and a second rear strap 704. In some embodiments, the first rear strap 702 is the rear top strap 260, and the second rear strap 704 is the rear bottom strap 262 shown in FIG. 2. In some embodiments, the first rear strap 702 has a first end and a second end. The second rear strap 704 may have a first end 705, a second end 707, and a length in between 708. In some embodiments, the first rear strap first end and the second rear strap first end 705 are attached to the main body first side 214. In some embodiments, the first rear strap second end and the second rear strap second end 707 are configured to wrap around behind a user's heel when worn and be attached to the main body second side 216. The first rear strap 702 may be configured to connect the main body first side panel 222 to the second panel 224 and form the rear 220 of the main body. In some embodiments, the second rear strap 704 may attach to the main body second side 216 to form a heel lock. For example, the second rear strap first end 705 may be connected to the main body first side 214 and cross behind a user's Achilles tendon and attach to the main body second panel 216. The independent heel lock stability strap allows for personalized volume fit and suitable compression at the Achilles tendon and enhances inversion support to a user's ankle.

In some embodiments, the first rear strap 702 and the second rear strap 704 may be attached to the main body 200 using any suitable connection or coupling assembly. For example, the first rear strap 702 and the second rear strap 704 may be attached to the main body using a hook and loop fastener such as that sold under the trade name Velcro®.

Figure 14:
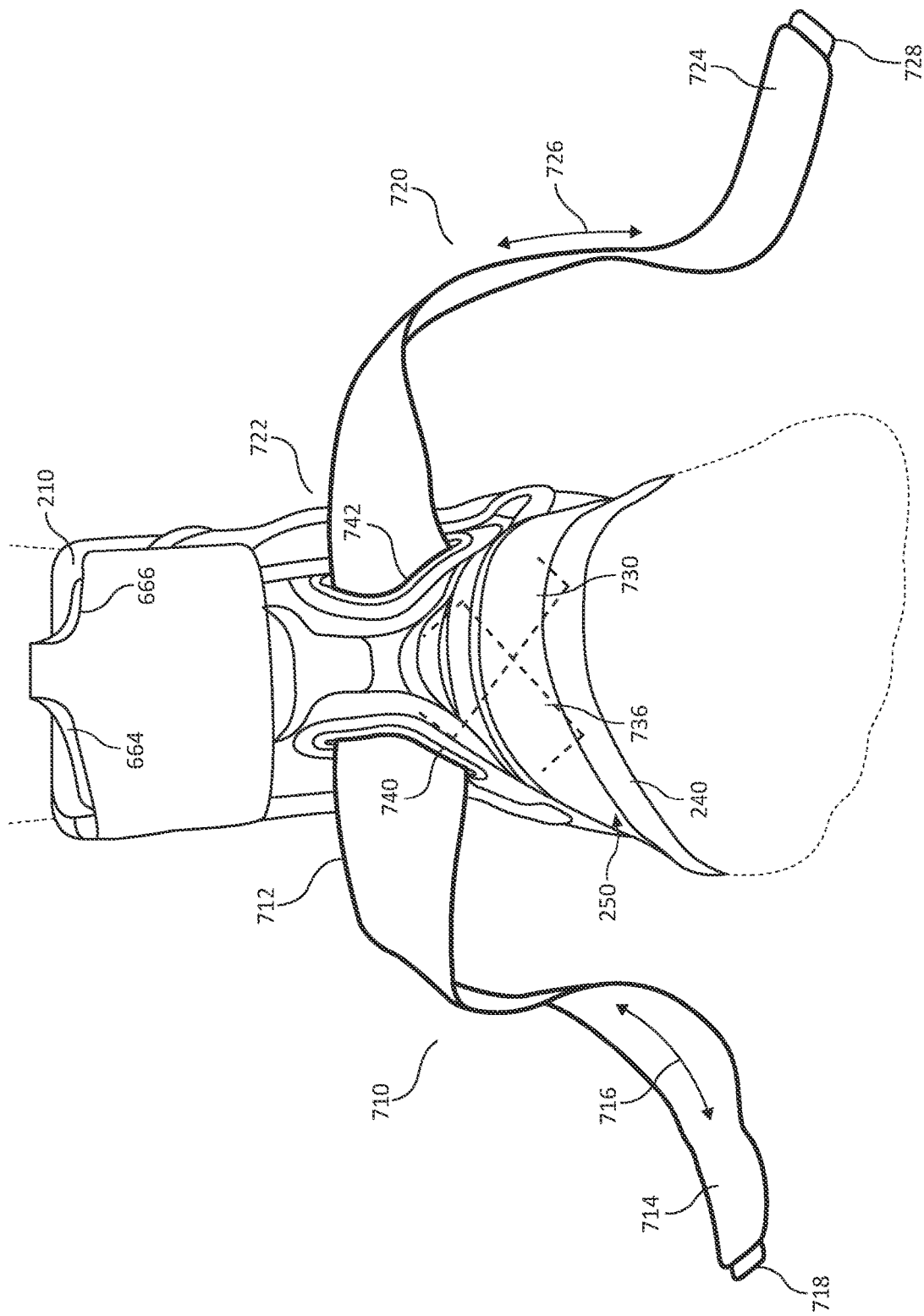
FIG. 14 is a front view of an embodiment of an ankle brace, showing a strap assembly.

FIG. 14 is a front view of the ankle brace system 100 showing features of the strap assembly 120 including the first cross strap 710, and the second cross strap 720. The first cross strap 710 includes a first end 712, a second end 714, and a length 716 in between. The second cross strap 720 includes a first end 722, a second end 724, and a length 726 in between. A portion 730 of the first strap first end 712 may be hidden from view in FIG. 14. A portion 736 of the second strap first end 722 may be hidden from view in FIG. 14. For example, in some embodiments, the first cross strap first end 712 and second cross strap first end 722 may be attached to the main body 200 within at least a portion of the foot sleeve 240. That is, the first cross strap first end 712 and second cross strap first end 722 may be attached to the main body 200 underneath the main body outer surface 250.

In some embodiments, the first and second cross straps 710, 720 may be attached to the main body outer surface 250. In some embodiments, the main body may include openings 740, 742 to pass the first and second cross straps 710, 720 through. For example, the first cross strap first end 712 may be attached to the foot sleeve 240 underneath the outer surface 250 of the main body 200. The first cross strap length 716 may extend through the first opening 740 and extend toward the first side 214 of the main body. The second cross strap first end 722 may be attached to the foot sleeve 240 underneath the outer surface 250 of the main body 200. The second cross strap length 726 may extend through the second opening 742 and extend toward the second side 216 of the main body 200. Such a configuration may provide user's ankle or foot with suitable support, while maintaining the first and second cross straps 710, 720 in a position that it easier for a user to use. Such a configuration may also reduce the number of loose straps on the outer surface 250 that may interfere with a user's movement.

As shown in FIG. 14, in some embodiments, the first and second cross straps 710, 720 may include color tabs 718, 728. For example, the first cross strap 710 may include a first color tab 718 located toward the second end 714. The second cross strap 720 may include a second color tab 728 located toward the second end 724.

Figure 15:
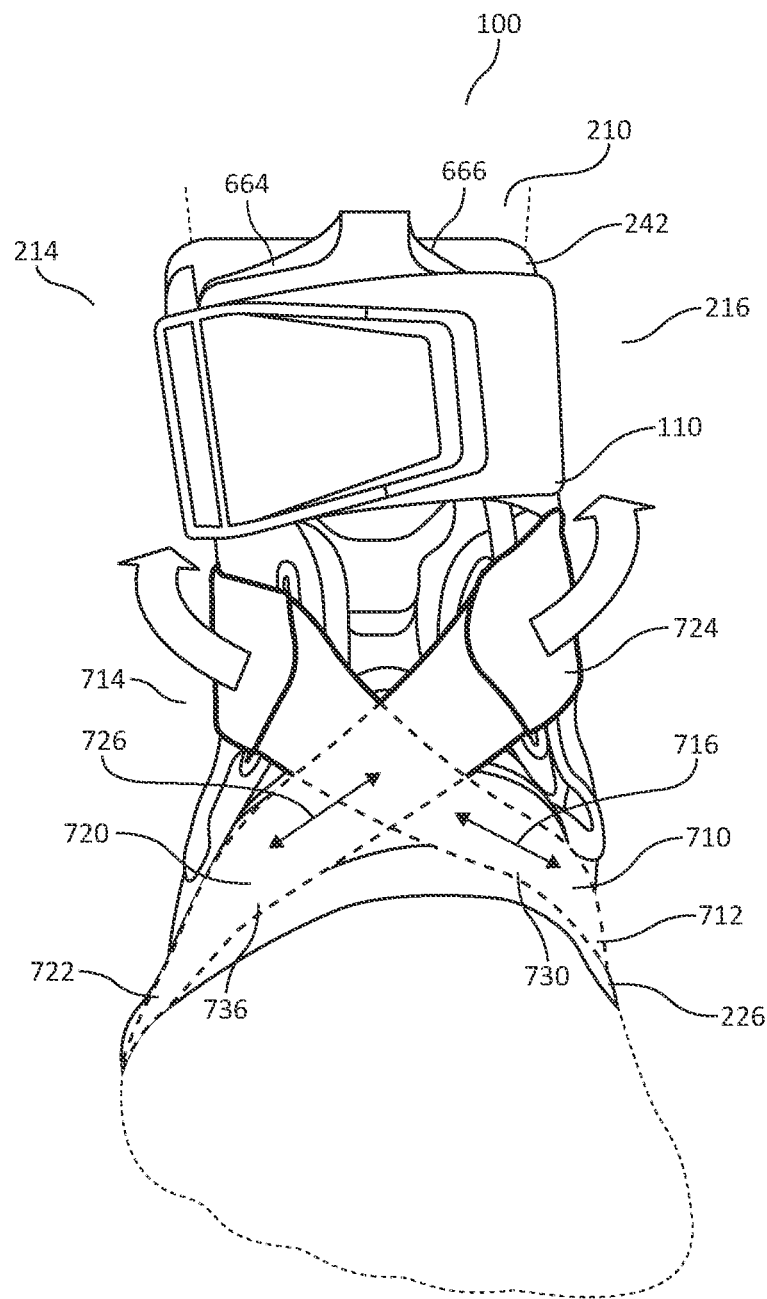
FIG. 15 is a front view of an embodiment of an ankle brace, showing a strap assembly.

FIG. 15 is a front view of the ankle brace system 100 showing the first and second cross straps second ends 714, 724 attached to the main body 200. As shown in FIG. 15, in some embodiments, the first cross strap first end 712 may be attached near the bottom panel 226 on the main body second side 216. Portions 730, 736 of the first and second first ends 712, 722 that are hidden from view in FIG. 14 are shown in broken lines in FIG. 15 to illustrate portions 730, 736 of the first and second cross straps 710, 720 that are within the main body 200 as described with reference to FIG. 14. The first cross strap 710 may extend over the foot sleeve 240, and wrap around behind a user's leg, with the second end 714 configured to attach to the top of the main body 200 on the second side 216. In some embodiments the first cross strap second end 714 is configured to attach toward the top 210 of the main body 200 along the leg sleeve 242. The second cross strap 720 may include a first end 722 attached to the bottom panel 226 on the main body first side 214, and wrap around behind a user's leg with the second end 724 attached to the main body 200 on the first side 214 (shown below in FIG. 16). In some embodiments, the second cross strap second end 724 is configured to attach toward the top 210 of the main body 200 along the leg sleeve 242.

Figure 16:
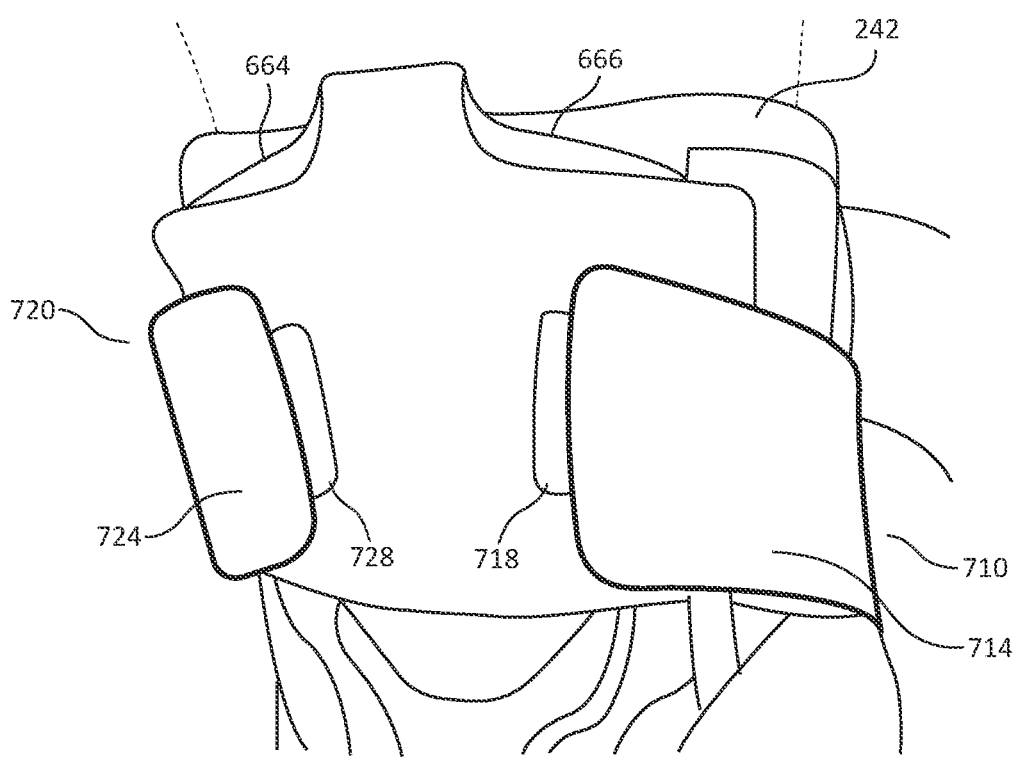
FIG. 16 is a front view of part of an embodiment of an ankle brace, showing a strap assembly.

FIG. 16 is a front view of the leg sleeve 242 showing the first and second cross straps second ends 714, 724 attached to the leg sleeve 242. In some embodiments, the color tabs 718, 728 on the first and second cross straps second ends 714, 724 may be matched with the colored sections 664, 666 on the top 210 of the main body. For example, colored sections 664, 666 on the top 210 of the main body 200 may be provided with a matching color to the color tab 718, 728 attached to the strap that is configured to be attached. Such a design may provide a visual indicator for a user to recognize where to attach the first and second cross straps second ends 714, 724 by attaching them to either of the colored sections 664, 666 having the same color. In some embodiments, the first and second cross straps second ends 714, 724 may be colored instead of, or in addition to, the color tabs 718, 728.

In some embodiments, the combined shape of the first and second cross straps 710, 712 after attaching to the main body 200 may form a substantially figure-8 starting under a user's foot and ending behind the user's leg. A figure-8 configuration may be constructed to wrap above a user's lateral and medial malleolus and provide compression support of the first and second internal supports 310, 312 and first and second external supports 610, 612 which may maximize inversion and over extension stability support of the ankle joint.

Using this configuration, the strap assembly 120 may be used to form an adjustable connection between the foot sleeve 240 and the leg sleeve 242 and the additional support structures described above. The first and second cross straps 710, 712 may be attached to the main body 200, for example, at the leg sleeve 242, using any suitable connection or coupling assembly. For example, the first and second cross straps second ends 714, 724 may be attached to the main body 200 using a clasp or clamp. In some embodiment, the first and second cross straps second ends 714, 724 may be attached to the main body 20 using a hook and loop fastener such as that sold under the trade name Velcro®. In some embodiments, the first and second cross straps 710, 712 may be color coded to allow a user to identify strap placement. For example, the first and second cross straps 710, 712 may include color coded tabs and the main body 200 may also include color coded attachment points for convenient and consistent strap positioning.

Figure 17:
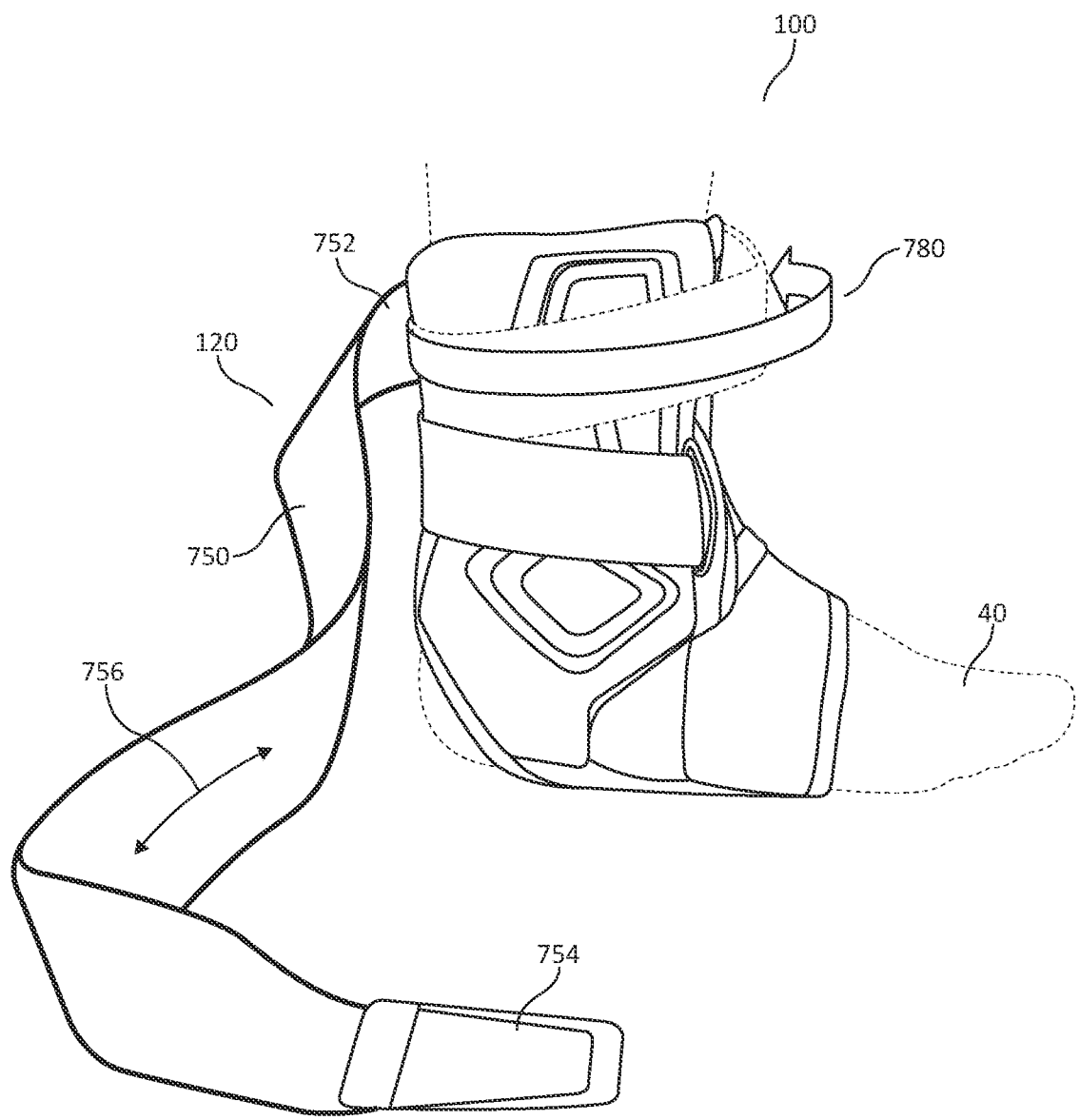
FIG. 17 is a side view of an embodiment of an ankle brace, showing a strap assembly.

FIG. 17 is a side view of the ankle brace system 100 on a wearer's foot 40 showing the top strap 750. In some embodiments, the top strap 750 is configured to be situated in the area indicated by the dotted lines and wrap around the leg sleeve 242 in the direction indicated by the arrow 780. In some embodiments, the top strap 750 has a first end 752, a second end 754, and a length 756 in between. In some embodiments, the top strap 750 may be pre-curved. For example, the top strap 750 may have a first and second side along the length 756, with one of the first or second side longer than the other, creating a pre-curved configuration in the top strap length 756. In some embodiments, the top strap 750 may be pre-curved to create a suitable fit around the leg and/or ankle of a user when worn.

Figure 18:
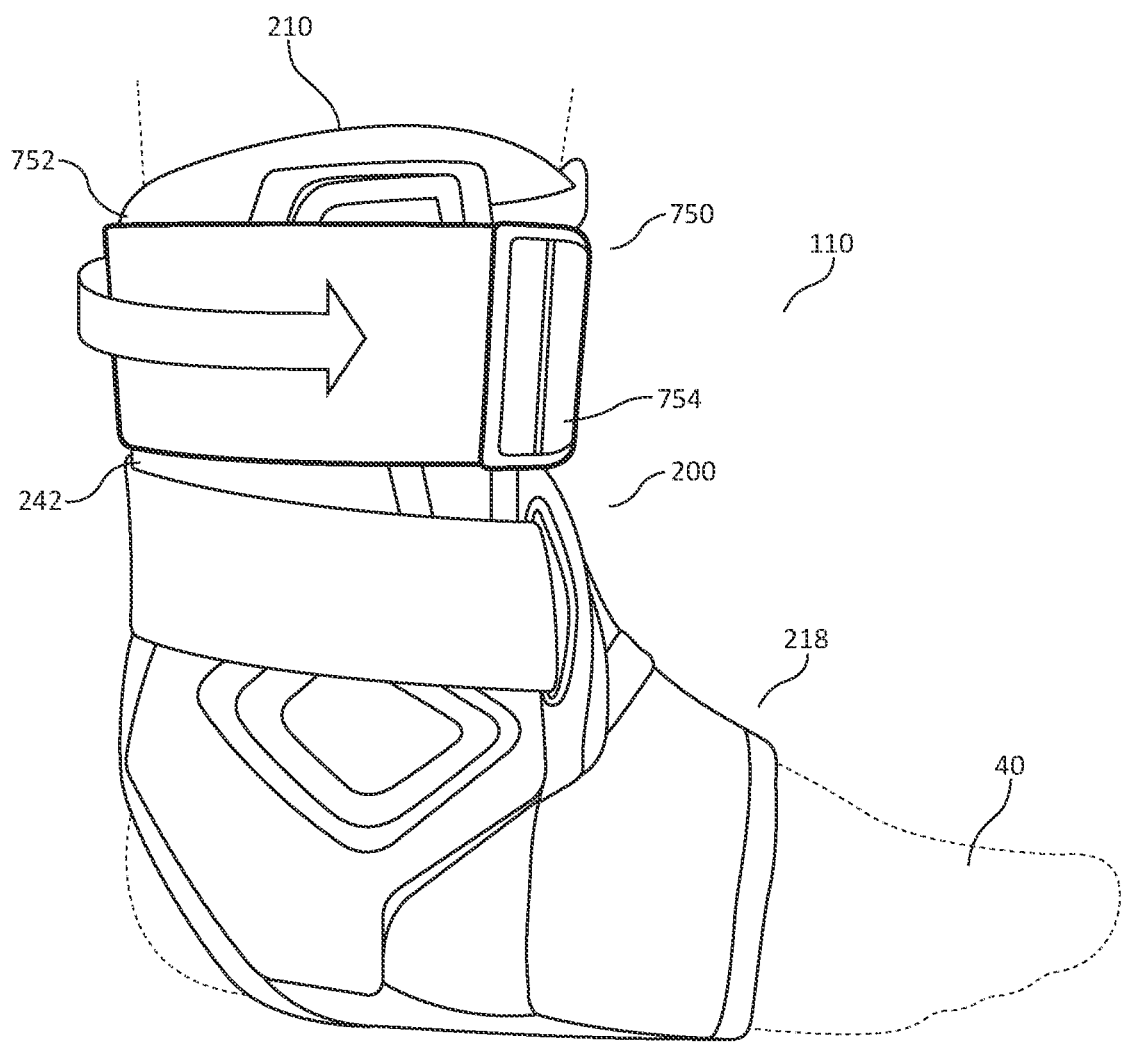
FIG. 18 is a side view of an embodiment of an ankle brace, showing a strap assembly.
Figure 19:
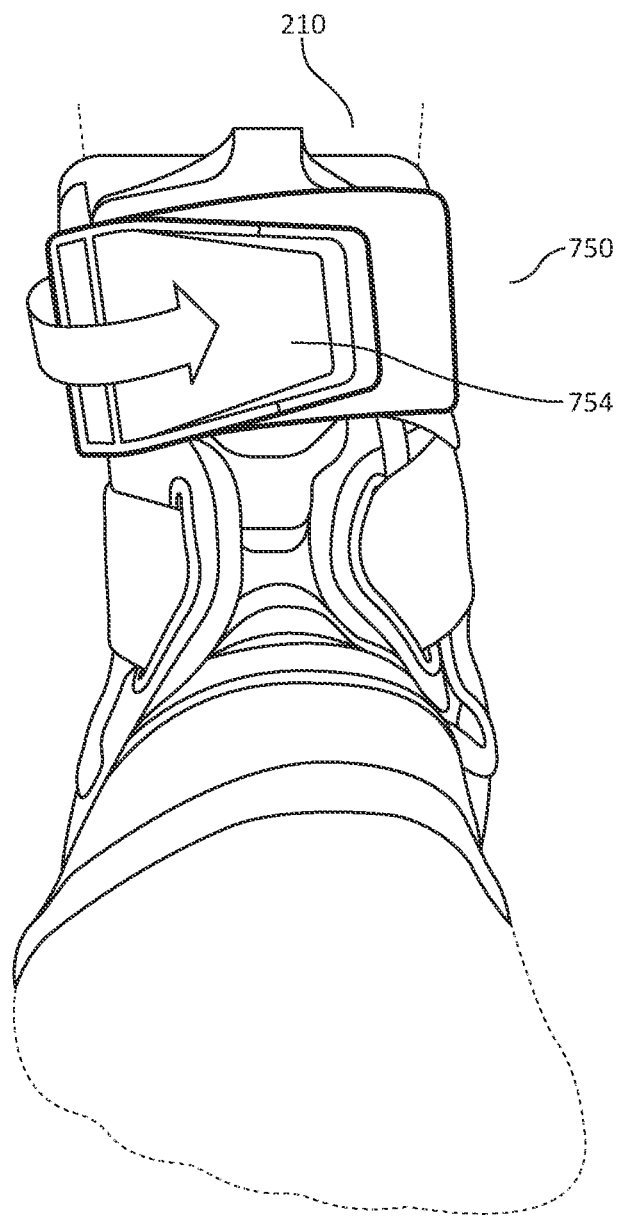
FIG. 19 is a front view of an embodiment of an ankle brace, showing a strap assembly.

FIGS. 18 and 19 show the top strap 750 in a strapped or wrapped configuration around the wrap assembly 110. In some embodiments, the first end 752 of the top strap 750 may be attached along the main body 200. The first end 752 of the top strap 750 may be attached at any suitable location, such as the leg sleeve 242 toward the front 218 of the wrap assembly 200. In some embodiments, the top strap 750 is configured to be wrapped around a leg of a user above the ankle bone. The top strap second end 754 may be attached along the main body 200. Alternatively, the top strap second end 754 may be wrapped around the leg sleeve 242. The top strap 750 may be wrapped around the first and second cross strap second ends 714, 72 to prevent potential detachment of the cross straps 710, 712 and may provide additional compression support at the top of the main body 200.

Although described above with regard to embodiments having multiple support features, it is also envisioned the ankle brace system 100 may be formed in certain embodiments having various features included or removed in various combinations. For example, it is envisioned that the main body 200 described in FIGS. 2 to 12 may be formed having various combinations of the first and second pads 270, 272; the first and second internal supports 310, 312; the bottom support 510; and the first and second external supports 610, 612. That is, the ankle brace system 100 may include all the above disclosed feature or may in some embodiments include only certain of these features in various combinations.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The following is claimed:

1. An ankle brace comprising:
an ankle wrap assembly including a main body having an inner surface, an outer surface, a top, a bottom, a front defining a foot opening, a first side panel, a second side panel, a rear, and a bottom panel;
first and second ankle pads attached to the main body;
a first support attached to the main body first side panel, a second support attached to the main body second side panel, and a bottom support, the bottom support having a first end, a second end, and a length in between, and wherein the bottom support first end is located adjacent a lateral side of a user's ankle, the length extends under the user's foot, and the second end is located adjacent a medial side of the user's ankle when worn by the user, wherein the bottom support is configured to allow the first and second supports to rotate in relation to the bottom support first and second ends;
wherein the ankle brace is configured to be secured to the user's ankle when worn.

2. The ankle brace of claim 1, wherein the first and second ankle pads are shaped to support the lateral and medial malleolus bones, respectively.

3. The ankle brace of claim 1, wherein the first and second supports include rigid support shells shaped to conform to the lateral and medial sides of the user's ankle, respectively, each of the first and second supports include a top portion fixed to the main body and a bottom portion suspended from the main body, and the first and second supports defining openings for the user's medial and lateral malleolus, respectively.

4. The ankle brace of claim 1, further comprising an anti-slip pad on the outer surface of the bottom panel.

5. The ankle brace of claim 1, further comprising first and second external supports fixed to the outer surface of the main body along the first side panel and the second side panel.

6. The ankle brace of claim 1, further comprising a strap system including a first rear strap, a second rear strap, a first cross strap, a second cross strap, and a top strap, wherein the first rear strap includes a heel lock strap having a first end connected to the ankle wrap main body first panel and configured to cross behind the user's Achilles tendon and a second end configured to attach to the ankle wrap main body second panel when worn by the user.

7. The ankle brace of claim 6, wherein the first cross strap includes a first end attached to the bottom panel on the ankle wrap first side, is configured to be placed across the front of the ankle wrap and around the back of the user's leg, and includes a second end having a first colored tab and configured to attach to the top of the ankle wrap on the first side of the main body at a location adjacent a first colored portion, and wherein the second cross strap includes a first end attached to the bottom panel on the ankle wrap second side, is configured to be placed across the front of the ankle wrap and around the back of the user's leg, and includes a second end having a second colored tab and configured to attach to the top of the ankle wrap on the second side of the main body at a location adjacent a second colored portion, when worn by the user.

8. The ankle brace of claim 6, wherein the top strap has a first end and a second end, and is configured to be placed around the top of the ankle wrap around a leg of the user above the ankle bone when worn, and wherein the top strap is pre-curved.

9. An ankle brace system comprising:
an ankle wrap configured to receive the ankle of a user, and including a main body having an inner surface, an outer surface, a top, a bottom, a front defining a forefoot sleeve, a lateral side panel, a medial side panel, a rear defining a rear opening, and a bottom panel;
at least one of first and second ankle pads on the ankle wrap inner surface; first and second internal supports; a bottom support; and first and second external supports, the first and second internal supports comprising plates shaped to conform to the lateral and medial sides of the ankle of the user, each of the first and second internal supports include a top portion fixed to the main body and a bottom portion suspended from the main body, and the first and second internal supports defining openings for the user's medial and lateral malleolus, respectively; and a strap system including a lower rear strap, an upper rear strap, a first cross strap, a second cross strap, and an ankle strap.

10. The ankle brace system of claim 9, wherein the first and second ankle pads are shaped to conform to the outer surface of the user's ankle adjacent the lateral and medial malleolus bones, respectively.

11. The ankle brace system of claim 9, wherein the lower rear strap comprises a heel lock strap having a first end connected to the lateral side panel and configured to cross behind the user's Achilles tendon and a second end configured to attach to the medial side panel.

12. The ankle brace system of claim 9, wherein the bottom support has a first end, a second end, and a length in between, and wherein the first end is located adjacent a lateral side of the user's ankle, the length extends under the user's foot, and the second end is located adjacent a medial side of the user's ankle when worn by the user.

13. The ankle brace system of claim 12, wherein the bottom support first end is configured to overlap with a portion of the first internal support and the bottom support second end is configured to overlap with a portion of the second internal support.

14. The ankle brace system of claim 9, wherein the ankle strap has a first end and a second end, and is configured to extend around the top of the ankle wrap around a leg of the user above the ankle bone when worn, and wherein the ankle strap is pre-curved.

15. The ankle brace system of claim 9, further comprising an anti-slip pad on the outer surface of the ankle wrap bottom panel.

16. An ankle brace system comprising a main body configured to receive an ankle and a portion of a foot of a user, the main body including an outer surface, and inner surface, a front defining a foot sleeve, a lateral panel, a medial panel, a rear portion defining an opening to receive the foot of the user, a top defining an ankle sleeve, and a bottom panel;

a medial malleolus pad and a lateral malleolus pad attached to the inner surface of the main body;

an internal support assembly including a lateral support plate having a top and bottom, a medial support plate having a top and bottom, and a bottom support configured to extend along the bottom panel, and having a first end overlapping the lateral support plate bottom, and a second end overlapping the lateral support plate bottom; and a strap assembly including a first and second cross strap, a first and second rear strap, and an ankle strap.

17. The ankle brace system of claim 16, wherein the lateral and medal support plates are shaped to conform to the outer surface of the user's ankle adjacent the lateral and medial malleolus bones, each of the lateral and medal support plates include a top portion fixed to the main body and a bottom portion not directly attached to the main body, and wherein the lateral support plate defines an opening shaped to support the user's lateral malleolus bone and the medial support plate defines an opening shaped to support the user's medial malleolus bone.

18. The ankle brace system of claim 16, wherein the bottom support first and second ends are shaped to receive the lateral and medial plates in a conforming fit and allow the lateral and medial plates to rotate relative to the bottom support when the ankle brace system is worn by the user.

\* \* \* \* \*